United States Patent [19]
Matsuoka et al.

[11] Patent Number: 5,932,454
[45] Date of Patent: Aug. 3, 1999

[54] METHOD OF PRODUCING CARBOXYLIC ACIDS

[75] Inventors: Kazuyuki Matsuoka, Kitakatsuragi-gun; Akinobu Matsuyama, Tsukuba, both of Japan

[73] Assignee: Daicel Chemical Industries, Ltd., Osaka, Japan

[21] Appl. No.: 08/992,545

[22] Filed: Dec. 17, 1997

[30] Foreign Application Priority Data

Dec. 20, 1996 [JP] Japan .................................. 8-341673

[51] Int. Cl.⁶ .............................. C12P 13/02; C12P 11/00
[52] U.S. Cl. .......................... 435/130; 435/129; 435/136; 435/822
[58] Field of Search ..................... 435/129, 130, 435/136, 822

[56] References Cited

U.S. PATENT DOCUMENTS

| | | | |
|---|---|---|---|
| 5,034,105 | 7/1991 | Berglund et al. | 435/136 |
| 5,166,426 | 11/1992 | Jakob et al. | 562/567 |
| 5,763,652 | 6/1998 | Kawabe et al. | 562/512 |
| 5,814,497 | 9/1998 | Favre-Bulle et al. | 435/130 |
| 5,814,508 | 9/1998 | Di Cosimo et al. | 435/227 |

FOREIGN PATENT DOCUMENTS

| | | |
|---|---|---|
| 58-15120 | 3/1983 | Japan . |
| 61-56086 | 3/1986 | Japan . |
| 2-84198 | 3/1990 | Japan . |
| 4-40898 | 2/1992 | Japan . |

OTHER PUBLICATIONS

APS Computer Abstract JPOABS Japan 08–245495 Kawabe "Production of Carboxylic Acid", Sep. 24, 1996.

*Primary Examiner*—Herbert J. Lilling
*Attorney, Agent, or Firm*—Birch, Stewart, Kolasch & Birch, LLP

[57] ABSTRACT

The method comprises (1) a carboxylic acid salt providing step comprising permitting a strain of microorganism or a preparation derived from the microorganism to act upon a nitrile to thereby (a) provide at least the corresponding amide which is then hydrolyzed in the presence of a base to provide a salt of the corresponding carboxylic acid or (b) provide a salt of the corresponding carboxylic acid and (2) an electrodialysis step comprising subjecting the carboxylic acid salt provided in the step (1) to electrodialysis to provide the corresponding carboxylic acid and base. Carboxylic acids can be produced without formation of ammonium hydrogen sulfate and other byproducts. The microorganism includes microorganisms of the genera Pantoea and Gordona. The ammonia formed in the step (1) can be reused as a nitrogen source in a nitrile production line.

26 Claims, 2 Drawing Sheets

METHOD OF PRODUCING CARBOXYLIC ACIDS

METHOD OF PRODUCING CARBOXYLIC ACIDS

The present invention relates to a method of producing a carboxylic acid from the corresponding nitrile. Carboxylic acids are compounds of great importance in the field of organic synthesis and have been produced in large quantities whether as synthetic intermediates or as end products.

BACKGROUND OF THE INVENTION

In the production of carboxylic acids by hydrolysis of nitrites, it is common practice to use sulfuric acid as a catalyst. In this technology, however, as can be seen from the following reaction formula (a), the nitrile compound reacts with sulfuric acid to give the objective carboxylic acid and the byproduct ammonium hydrogen sulfate in an equimolar ratio.

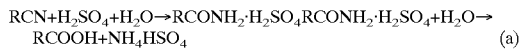

$$RCN+H_2SO_4+H_2O \rightarrow RCONH_2 \cdot H_2SO_4 RCONH_2 \cdot H_2SO_4+H_2O \rightarrow RCOOH+NH_4HSO_4 \qquad (a)$$

The byproduct ammonium hydrogen sulfate is discharged into the river or the like as an industrial waste. However, this effluent is detrimental to the earth's ecology and therefore presents problems. In addition, useful ammonia and sulfuric acid are not recovered but discarded, thus inflating the production cost and interfering with effective utilization of resources.

In recent years, energetic efforts have been made to develop a technology for treating processes of the byproduct ammonium hydrogen sulfate or a production process which would not give byproduct ammonium hydrogen sulfate. For example, there has been developed a process which, as illustrated in the following reaction scheme (b), comprises decomposing ammonium hydrogen sulfate thermally into nitrogen, SO$_2$, and water, oxidizing the SO$_2$ thus produced and recovering it in the form of sulfuric acid, and recycling the sulfuric acid as a catalyst for hydrolysis of nitrile compounds.

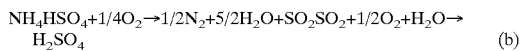

$$NH_4HSO_4+1/4O_2 \rightarrow 1/2N_2+5/2H_2O+SO_2 SO_2+1/2O_2+H_2O \rightarrow H_2SO_4 \qquad (b)$$

However, in this process, too, pyrolysis of ammonium hydrogen sulfate liberates nitrogen gas and does not permit recovery of ammonia. In addition, nitrogen oxides formed on pyrolysis of ammonium hydrogen sulfate contaminate the environment. Moreover, the process from pyrolysis of ammonium hydrogen sulfate to recovery of sulfuric acid involves many complicated steps which require additional capital investment. As a result, carboxylic acids can hardly be produced efficiently and at a low cost.

Meanwhile, there has been proposed a technology for hydrolyzing a nitrile to the corresponding carboxylic acid with the aid of microorganisms. For example, Japanese Patent Publication No. 15120/1983 (JP-B-58-15120) discloses a technology for converting lactonitrile and hydroxyacetonitrile to the corresponding carboxylic acids by means of a strain of microorganism belonging to the genus Bacillus, the genus Bacteridium, the genus Micrococcus, or the genus Brevibacterium. Reported in Journal of Fermentation Technology, 51, 393 (1973) is a method for causing a yeast of the genus Torulopsis to elaborate optically active L-α-hydroxyvalerianic acid and L-α-hydroxyisocaproic acid from α-hydroxynitrile. Japanese Patent Application Laid-open No. 56086/1986 (JP-A-61-56086) discloses a technology employing a microorganism of the genus Corynebacterium to convert glyconitrile, lactonitrile and acetonecyanohydrin to the corresponding α-hydroxy acids. Japanese Patent Application Laid-open No. 84198/1990 (JP-A-2-84198) discloses a method for producing an optically active α-hydroxy acid from the corresponding α-hydroxynitrile by means of a microorganism belonging to the genus Alcaligenes, the genus Pseudomonas, the genus Rhodopseudomonas, the genus Corynebacterium, the genus Acinetobacter, the genus Bacillus, the genus Mycobacterium, the genus Rhodococcus, or the genus Candida. Japanese Patent Application Laid-open No. 40898/1992 (JP-A-4-40898) describes a method for converting α-hydroxy-4-methylthiobutyronitrile to α-hydroxy-4-methylthiobutyric acid by means of a microorganism belonging to the genus Caseobacter, the genus Pseudomonas, the genus Alcaligenes, the genus Corynebacterium, the genus Brevibacterium, the genus Nocardia, the genus Rhodococcus, or the genus Arthrobacter.

In those processes involving microorganisms, the product carboxylic acid usually forms a salt with the byproduct ammonia. When, for the purpose of isolating the free carboxylic acid from the salt, the salt is treated with an acid such as hydrochloric acid or sulfuric acid, the ammonium salt corresponding to the acid used, such as ammonium chloride or ammonium sulfate, is formed. Thus arising are problems comparable to those mentioned in connection with the technology using sulfuric acid as a catalyst.

SUMMARY OF THE INVENTION

It is, therefore, an object of the present invention to provide a method of producing carboxylic acids which does not give rise to byproducts such as ammonium hydrogen sulfate.

Another object of the invention is to provide a method of producing carboxylic acids which permits an easy and expedient recovery of the useful ammonia and catalyst.

A still further object of the invention is to provide a method of producing carboxylic acids which is conducive to effective utilization of the ammonia and catalyst substance.

The inventors of the present invention did intensive research to accomplish the above objects and found that when the hydration of nitriles with the aid of microorganisms and electrodialysis are used in combination, carboxylic acids can be produced without giving rise to byproducts such as ammonium hydrogen sulfate. They have accordingly perfected the instant invention.

The method of producing carboxylic acids in accordance with this invention, therefore, comprises (1) a carboxylic acid salt providing step comprising permitting a strain of microorganism capable of hydrating nitrites or a preparation derived from the microorganism to act upon a nitrile to (a) provide at least the corresponding amide which is then hydrolyzed in the presence of a base to the corresponding carboxylic acid salt or (b) provide the corresponding carboxylic acid salt and (2) an electrodialysis step comprising subjecting the carboxylic acid salt formed in the carboxylic acid salt providing step to electrodialysis to provide the corresponding carboxylic acid and base.

The nitrile mentioned above includes but is not limited to cyanohydrin compounds. The microorganism capable of hydrating nitrites includes but is not limited to microorganisms belonging to the genus Pantoea, the genus Micrococcus, the genus Bacteridium, the genus Bacillus, or the genus Gordona. The base that can be used includes alkali metal hydroxides, among others. The electrodialysis can be typically carried out using an electrodialyzer comprising a bipolar membrane and at least one ion exchange membrane selected from cation exchange membranes or anion exchange membranes.

The above production process may further comprise (3) a step of recycling the reaction mixture obtained by permitting the strain of microorganism or the preparation derived therefrom to act upon the nitrile to the hydration reaction system of the carboxylic acid salt providing step, (4) an amide extraction step for extracting the amide into an organic solvent from the amide-containing reaction mixture obtained by permitting the strain of microorganism or the preparation derived therefrom to act upon the nitrile, (5) a concentration step for concentrating a reaction mixture containing the product amide or carboxylic acid salt as obtained by permitting the strain of microorganism or the preparation derived therefrom to act upon the nitrile, or a. reaction mixture containing the product carboxylic acid salt as obtained by hydrolysis of the amide, (6) an ammonia recovery step for recovering the ammonia byproduced in carboxylic acid salt providing step (1), (7) a step of utilizing the recovered ammonia as a nitrogen source in a nitrile production line, (8) a carboxylic acid extraction step for extracting the carboxylic acid into an organic solvent from a mixture containing the carboxylic acid and water as formed in electrodialysis step (2), (9) a carboxylic acid separating step for separating the carboxylic acid and the organic solvent, respectively, from an organic phase or layer as provided in carboxylic acid extraction step (8), (10) a step of recycling the organic solvent separated in carboxylic acid separating step (9) for reuse as an extraction solvent for carboxylic acid extraction step (8) or amide extraction step (4), (11) a step of reusing the base formed in electrodialysis step (2) as the base for carboxylic acid salt providing step (1), and (12) a step of subjecting the ammonium carboxylate produced in carboxylic acid salt providing step (1) to a salt exchange reaction with a base.

BRIEF DESCRIPTION OF THE DRAWINGS

The present invention is now described in detail, reference being made, where necessary, to the accompanying drawings, wherein.

DETAILED DESCRIPTION OF THE INVENTION

[Nitrile]

Figure 1:
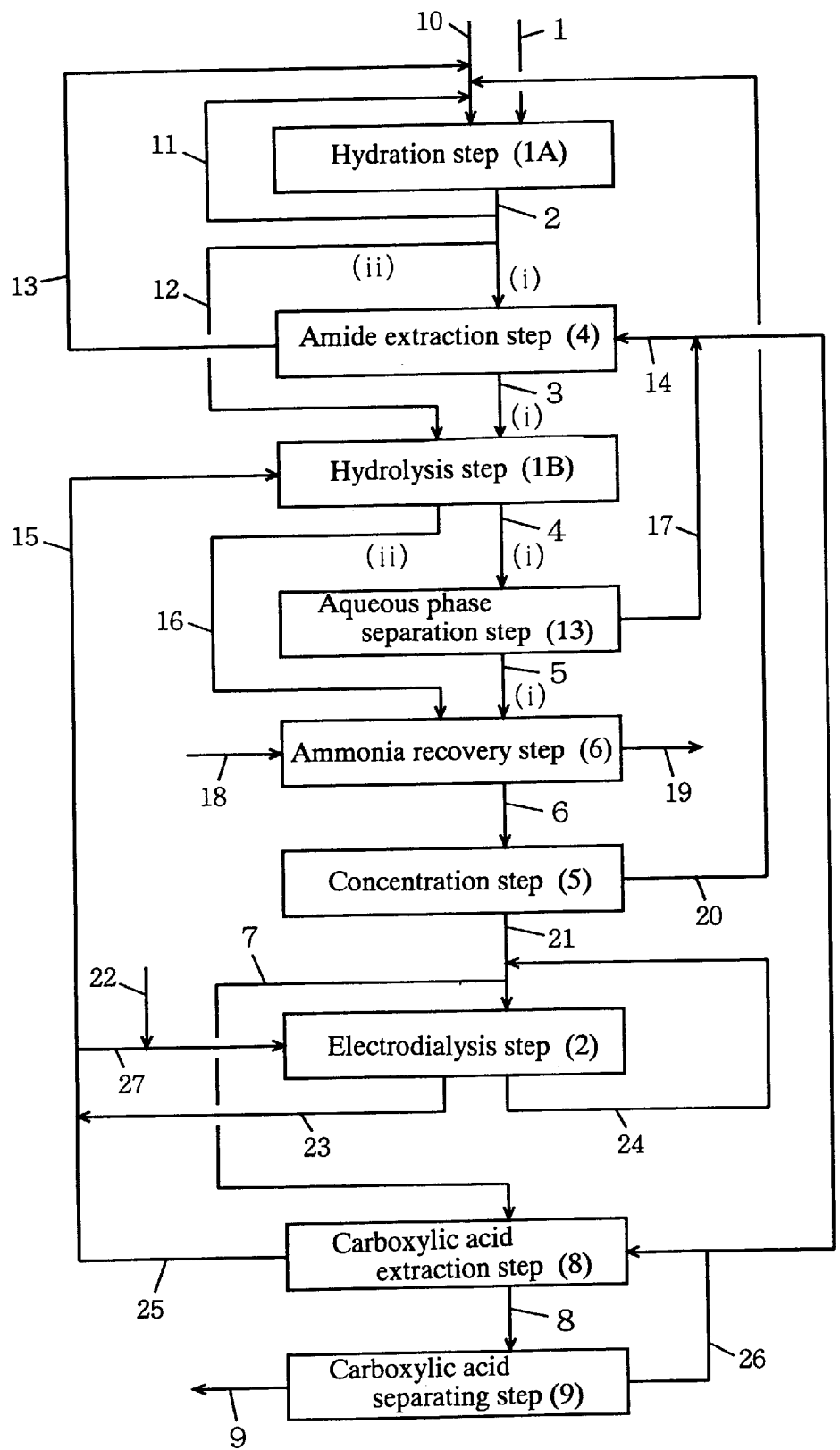
FIG. 1 is a flow diagram of an example of carboxylic acid production technology according to the invention.

The species of nitrile that can be used in the practice of the present invention is not particularly limited but can be liberally selected from a broad range of compounds. The nitrile can be typically represented by the formula RCN or the formula RCOCN (wherein R represents an aliphatic hydrocarbon group, an alicyclic hydrocarbon group, an aromatic hydrocarbon group, or a heterocyclic group, which group may have at least one substituent. The nitrile includes polynitriles. Thus, the aliphatic hydrocarbon group, alicyclic hydrocarbon group, aromatic hydrocarbon group, or heterocyclic group is not limited to a univalent group but may be a bi- or multivalent group.

The aliphatic hydrocarbon group mentioned above includes saturated hydrocarbon groups and unsaturated hydrocarbon groups, e.g. alkyl groups each containing 1 to about 12 carbon atoms (preferably 1 to 6 carbon atoms), such as methyl, ethyl, propyl, isopropyl, butyl, isobutyl, s-butyl, t-butyl, pentyl, hexyl, octyl, decyl, etc.; alkenyl groups each containing 2 to about 12 carbon atoms, such as vinyl, allyl, 1-propenyl, isopropenyl, 2-butenyl, etc.; alkinyl groups each containing 2 to about 12 carbon atoms, such as ethinyl, 2-propinyl, etc.; and alkylene groups each containing 2 to about 12 carbon atoms.

The alicyclic hydrocarbon group includes cycloalkyl groups each containing 3 to about 10 carbon atoms, such as cyclopropyl, cyclobutyl, cyclopentyl, cyclohexyl, cyclooctyl, etc. and the corresponding cycloalkylene groups. The aromatic hydrocarbon group includes aryl groups each containing 6 to about 14 carbon atoms, such as phenyl, naphthyl, etc. and the corresponding arylene groups.

The heterocyclic group includes heterocyclic groups each containing at least one hetero-atom selected from among nitrogen, oxygen, and sulfur atoms. The heterocyclic group may be an aromatic heterocyclic (heteroaromatic) group, a nonaromatic heterocyclic group, or a fused or condensed heterocyclic group. The heterocyclic group thus includes but is not limited to furyl, thienyl, pyrrolyl, pyrrolidinyl, pyridyl, pyrazinyl, pyrimidinyl, pyridazinyl, piperidino, morpholino, morpholinyl, and quinolyl.

The group represented by R may, in turn, have such substituents as halogen atom, hydroxy, alkyl (e.g. $C_{1-5}$ alkyl such as methyl, ethyl, propyl, isopropyl, etc.), aryl (e.g. $C_{6-14}$ aryl such as phenyl, tolyl, xylyl, chlorophenyl, methoxyphenyl, naphthyl, etc.), ether, alkoxy (e.g. $C_{1-5}$ alkoxy such as methoxy, ethoxy, etc.), aryloxy (e.g. $C_{6-14}$ aryloxy such as phenoxy etc.), mercapto, alkylthio (e.g. $C_{1-5}$ alkylthio such as methylthio, ethylthio, etc.), arylthio (e.g. $C_{6-14}$ arylthio such as phenylthio etc.), carboxy, ester (e.g. $C_{1-6}$ alkoxycarbonyl such as methoxycarbonyl etc. and $C_{2-12}$ acyloxy such as acetoxy etc.), acyl (e.g $C_{2-12}$ acyl such as acetyl, benzoyl, etc.), amino, mono- or disubstituted amino (e.g. mono- or disubstituted $C_{1-5}$ alkylamino such as methylamino, dimethylamino, etc.), and nitro, among others. The number of substituents may for example be 1 to about 4.

The aliphatic nitrile includes but is not limited to saturated or unsaturated nitriles each containing 2 to 6 carbon atoms (e.g. saturated mononitriles such as acetonitrile, propionitrile, butyronitrile, isobutyronitrile, valeronitrile, isovaleronitrile, etc.; saturated dinitriles such as malonitrile, adiponitrile, etc.; and unsaturated nitriles such as acrylonitrile, methacrylonitrile, allyl cyanide, crotonitrile, etc.). The aliphatic nitrile further includes compounds of the formula RCOCN (R has the same meaning as defined hereinbefore), such as pyruvonitrile.

The alicyclic nitrile includes, for example, nitriles each containing 4 to 10 carbon atoms (e.g. cyclopentanecarbonitrile, cyclohexanecarbonitrile, etc.).

The aromatic nitrile includes but is not limited to aromatic mononitriles such as benzonitrile, o-, m-, and p-chlorobenzonitrile, o-, m-, and p-fluorobenzonitrile, o-, m-, and p-nitrobenzonitrile, o-, m-, and p-tolubenzonitrile, 2,4-dichlorobenzonitrile, anisonitrile, α-naphthonitrile, β-naphthonitrile, etc. and aromatic dinitriles such as phthalonitrile, isophthalonitrile, and terephthalonitrile, among others. The aromatic nitrile further includes aralkyl group-containing nitrites such as phenylacetonitrile, p-hydroxyphenylacetonitrile, p-methoxyphenylacetonitrile, and so on.

The heterocyclic nitrile includes nitrites each having a 5- or 6-membered ring containing at least one hetero-atom selected from among nitrogen, oxygen, and sulfur as a ring member, for example nitrites containing sulfur or oxygen as a hetero-atom, such as 2-thiophencarbonitrile, 2-furonitrile, etc.; nitriles containing nitrogen as a hetero-atom, such as 2-cyanopyridine, 3-cyanopyridine, 4-cyanopyridine, cyanopyrazine, cyanopiperidine, etc.; and fused heterocyclic nitriles such as 5-cyanoindole etc. The heterocyclic nitrile further includes compounds of the formula RCOCN (R represents a heterocyclic group), such as nicotinonitrile, isonicotinonitrile, etc.

The nitrile compound whose aliphatic hydrocarbon, alicyclic hydrocarbon, aromatic hydrocarbon, or heterocyclic moiety rep:resented by R is substituted includes, for example, aminonitrile compounds and cyanohydrin compounds. As aminonitrile compounds, there may be mentioned α-aminonitriles such as aminoacetonitrile, α-aminopropionitrile, α-aminobutyronitrile, etc. and β-aminonitriles such as 3-aminopropionitrile, etc.

The cyanohydrin compound includes α-cyanohydrin compounds, β-cyanohydrin compounds, and γ-cyanohydrin compounds. The carbon number of such a cyanohydrin compound may, for example, be 2 to 18, preferably 3 to 12, and more preferably about 3 to 8.

The α-cyanohydrin compound may for example be a compound of the following formula (Ia),

(Ia)

wherein $R^1$ and $R^2$ may be the same or different and each represents a hydrogen atom or a hydrocarbon group which may be substituted, or $R^1$ and $R^2$ may jointly form a ring in association with the adjacent carbon atom; provided that where $R^1$ represents a hydrogen atom, $R^2$ does not represent a hydrogen atom, and vice versa.

The hydrocarbon group or groups represented by $R^1$ and $R^2$ above and the substituent group or groups which may be present thereon include the same aliphatic hydrocarbon groups, alicyclic hydrocarbon groups, and aromatic hydrocarbon groups as mentioned hereinbefore in the definition of R and the same substituent groups as mentioned hereinbefore for these hydrocarbon groups.

Preferred examples of $R^1$ and $R^2$ include not only alkyl groups of 1 to about 12 carbon atoms (preferably $C_{1-6}$), alkenyl groups of 2 to about 12 carbon atoms, alkinyl groups of 2 to about 12 carbon atoms, cycloalkyl groups of 3 to about 10 carbon atoms, and aryl groups of 6 to about 14 carbon atoms, all of which have been mentioned in the definition of R, but also $C_{7-10}$ aralkyl groups such as phenylmethyl, 2-phenylethyl, 1-phenylethyl, 3-phenylpropyl, and 4-phenylbutyl, among others.

The above-mentioned ring which is optionally formed by $R^1$ and $R^2$ in association with the adjacent carbon atom includes cycloalkane rings of 3 to about 8 carbon atoms, such as cyclopropyl, cyclobutyl, cyclopentyl, cyclohexyl, cycloheptyl, and cyclooctyl.

The α-cyanohydrin compound typically includes aliphatic α-cyanohydrins such as hydroxyacetonitrile, lactonitrile, acetonecyanohydrin, 2-hydroxybutanenitrile, 2-hydroxy-4-methylthiobutanenitrile, 2-hydroxy-2-methylbutanenitrile, 2-hydroxy-3-methylbutanenitrile, 2-hydroxy-3-butenenitrile, 2-hydroxypentanenitrile, 2-hydroxyhexanenitrile, 2-hydroxyoctanenitrile, etc.; alicyclic α-cyanohydrins such as 2-hydroxycyclohexaneacetonitrile, cyclopentanonecyanohydrin, cyclohexanonecyanohydrin, etc.; and aromatic α-cyanohydrins such as mandelonitrile, 2-hydroxy-3-phenylbutanenitrile, and so on.

The β-cyanohydrin compound typically includes 3-hydroxypropanenitrile, 3-hydroxybutanenitrile, 3-hydroxyhexanenitrile, 2-hydroxycyclohexanecarbonitrile, and 3-hydroxy-3-phenylpropanenitrile, among others.

The γ-cyanohydrin compound includes but is not limited to 4-hydroxybutanenitrile, 4-hydroxyhexanenitrile, 3-hydroxyhexanecarbonitrile, and 4-hydroxy-4-phenylbutanenitrile, among others.

Since the electrodialysis step in accordance with the present invention is generally carried out in the presence of water, the above-mentioned nitrile is preferably a compound such that salts of the corresponding carboxylic acid will be water-soluble. From this point of view, the total carbon number of the nitrile may for example be about 2 to 18, preferably about 2 to 12, and more preferably about 2 to 8.

The preferred nitrile includes cyanohydrin compounds, particularly α-cyanohydrin compounds such as the above compounds of formula (Ia), which are useful for the production of hydroxycarboxylic acids. The still more preferred nitrile includes aliphatic α-cyanohydrins of about 3 to 8 carbon atoms, such as lactonitrile, acetonecyanohydrin, 2-hydroxy-4-methylthiobutanenitrile, etc.

The nitrites can be produced by the routine technology. An aliphatic nitrile, for instance, can be produced by reacting an alkyl halide or a dialkyl sulfate with an alkali cyanide such as potassium cyanide. An aromatic nitrile can be typically produced by a process which comprises diazotizing an amine and reacting the resulting diazo compound with copper (I) cyanide.

Among nitrile compounds, α-cyanohydrin compounds in particular can be produced by a process which comprises permitting hydrogen cyanide to act on an aldehyde or ketone or a process which comprises permitting an alkali cyanide such as potassium cyanide to act on an aldehyde or ketone-sodium hydrosulfite adduct. β-Cyanohydrin compounds can be produced by reacting epoxides with hydrogen cyanide.

[The microorganism or a preparation derived therefrom]

The microorganism may be any microorganism capable of hydrating nitrites. The microorganism thus includes but is not limited to (1) the genus Pantoea, (2) the genus Micrococcus, (3) the genus Bacteridium, (4) the genus Bacillus, (5) the genus Actinomadura, (6) the genus Kitasatospora, (7) the genus Pilimelia, (8) the genus Achromobacter, (9) the genus Beijerinckia, (10) the genus Cellulomonas, (11) the genus Klebsiella, (12) the genus Actinopolispora, (13) the genus Actinosynnema, (14) the genus Actinopulanes, (15) the genus Amycolata, (16) the genus Saccharopolyspora, (17) the genus Streptomyces, (18) the genus Nocardioides, (19) the genus Providencia, (20) the genus Microbacterium, (21) the genus Rhodobacter, (22) the genus Rhodospirillum, (23) the genus Caseobacter, (24) the genus Pseudomonas, (25) the genus Alcaligenes, (26) the genus Corynebacterium, (27) the genus Brevibacterium, (28) the genus Nocardia, (29) the genus Rhodococcus, (30) the genus Arthrobacter, (31) the genus Torulopsis, (32) the genus Rhodopseudonionas, (33) the genus Acinetobacter, (34) the genus Mycobacterium, (35) the genus Candida, (36) the genus Agrobacterium, (37) the genus Aspergillus, (38) the genus Penicillium, (39) the genus Cochliobolus, (40) the genus Fusarium, (41) the genus Enterobacter, (42) the genus Xanthobacter, (43) the genus Erwinia, (44) the genus Citrobacter, (45) the genus Aeromonas, and (46) the genus Gordona.

Those microorganisms have at least one enzyme among nitrile hydratase which is the enzyme converting nitrites to amides, amidase which is the enzyme converting amides to carboxylic acids, and nitrilase which is the enzyme converting nitriles to carboxylic acids. Many of those microorganisms have a plurality of enzymes among the above-mentioned enzymes, for example nitrile hydratase and amidase.

Depending on the species of enzymes possessed by microorganisms, there are cases in which only amide compounds are produced, cases in which only carboxylic acids are produced, and cases in which amide compounds and carboxylic acids are both produced. When a strain of microorganism capable of producing a carboxylic acid or a preparation derived therefrom is permitted to act upon a nitrile, the carboxylic acid produced generally forms a salt with the byproduct ammonia.

The microorganism capable of acting on a nitrile to produce the corresponding carboxylic acid includes but is not limited to the following microorganisms.

(1) The genus Pantoea: *Pantoea Agglommerans* NH-3 (FERM P-11349), etc.
(2) The genus Micrococcus: Micrococcus sp. A111 (FERM P-2720), etc.
(3) The genus Bacteridium: Bacteridium sp. R341 (FERM P-2719), Bacteridium sp. R340 (FERM P-2718), etc.
(4) The genus Bacillus: Bacillus sp. R332 (FERM P-2717), Bacillus sp. R340,
Bacillus subtilisCN5 (FERM BP-2354), etc.
(5) The genus Actinomadura: *Actinomadura cremea* subsp. *cremea* IFO 14182, etc.
(6) The genus Kitasatospora: *Kitasatospora setae* IFO 14216, etc.
(7) The genus Pilimelia: *Pilimelia terevasa* IFO 14556, etc.
(8) The genus Achromobacter: *Achromobacter xerosis* IFO 12668, etc.
(9) The genus Beijerinckia: *Beijerinckia indica* subsp. *indica* IFO 3744, etc.
(10) The genus Cellulomonas: *Cellulomonas flavigena* IFO 3754, etc.
(11) The genus Klebsiella: *Klebsiella pneumoniae* subsp. *pneumoniae* NH-36 (FERM P-11739), etc.
(12) The genus Actinopolispora: *Actinopolispora halophila* IFO 14100, etc.
(13) The genus Actinosynnema: *Actinosynnema mirum* IFO 14064, etc.
(14) The genus Actinopulanes: *Actinopulanes lobatus* IFO 12513, etc.
(15) The genus Amycolata: *Amycolata autotrophica* IFO 12743, etc.
(16) The genus Saccharopolyspora: *Saccharopolyspora rectivigula* IFO 12134, etc.
(17) The genus Streptomyces: Streptomyces sp. IFO 13809, etc.
(18) The genus Nocardioides: *Nocardioides flavus* IFO 14396, etc.
(19) The genus Providencia: *Providencia stuartii* IFO 12930, etc.
(20) The genus Microbacterium: *Microbacterium lacticum* IFO 14135, etc.
(21) The genus Rhodobacter: *Rhodobacter spheroides* IFO 12203, etc.
(22) The genus Rhodospirillum: *Rhodospirillum rubrum* IFO 3986, etc.
(23) The genus Caseobacter: Caseobacter sp. BC23 (FERM P-11261), etc.
(24) The genus Pseudomonas: Pseudomonas sp. BC13-2 (FERM P-11266), Pseudomonas sp. B21C9 (FERM BP-3737), *Pseudomonas fluorescens* NRRL B-981 (IFO 3925), *Pseudomonas fluorescens* IFO 3081, *Pseudomonas vesicularis* ATCC 11426, etc.
(25) The genus Alcaligenes: Alcaligenes sp. BC35-2 (FERM P-11265), *Alcaligenes faecalis* ATCC 8750, etc.
(26) The genus Corynebacterium: *Corynebacterium nitrilophilus* ATCC 21419, Corynebacterium sp. KO-2-4 (FERM BP-2353), Corynebacterium sp. B-96 (FERM P-7733), Corynebacterium sp. C-99 (FERM P-7734), etc.
(27) The genus Brevibacterium: *Brevibacterium acetylicum* IAM 1790, *Brevibacterium imperiale* B-222 (FERM P-2721), Brevibacterium sp. R312 (FERM P-2722), Brevibacterium sp. C211 (FERM P-2723), etc.
(28) The genus Nocardia: Nocardia sp. N-775 (FERM P-4447), etc.
(29) The genus Rhodococcus: Rhodococcus sp. SK92 (FERM P-11305), Rhodococcus sp. AK32 (FERM BP-1046), etc.
(30) The genus Arthrobacter: Arthrobacter sp. HR4 (FERM P-11302), etc.
(31) The genus Torulopsis
(32) The genus Rhodopseudomonas: *Rhodopseudomonas sphaeroies* ATCC 11167, etc.
(33) The genus Acinetobacter: Acinetobacter sp. AK226 (FERM PBP-2451), etc.
(34) The genus Mycobacterium: Mycobacterium sp. AC777 (FERM BP-2352), etc.
(35) The genus Candida: *Candida tropicalis* ATCC 20311, etc.
(46) The genus Gordona: *Gordona rubropertinctus* JCM 3204, etc.

The microorganism capable of acting upon a nitrile to produce the corresponding amide includes but is not limited to the following microorganisms.

(2) The genus Micrococcus: Micrococcus sp. A111 (FERM P-2720), etc.
(3) The genus Bacteridium: Bacteridium sp. R341 (FERM P-2719), Bacteridium sp. R340 (FERM P-271.8), etc.
(4) The genus Bacillus: Bacillus sp. R332 (FERM P-2717), *Bacillus smithii* SC-J05-1 (FERM P-14037, FERM BP-4935), etc.
(20) The genus Microbacterium: *Microbacterium flovum* IAM 1642, etc.
(24) The genus Pseudomonas: Pseudomonas sp. SK87 (FERM P-11311), *Pseudomonas chlororaphis* B23 (FERM BP-187), Pseudomonas sp. PS1 (FERM BP-188), Pseudomonas sp. MY-1 (FERM P-9174), etc.
(25) The genus Alcaligenes: Alcaligenes sp. BC16-2 (FERM P-11276), etc.
(26) The genus Corynebacterium: *Corynebacterium nitrilophilus* ATCC 21419, Corynebacterium sp. N-771 (FERM P-4445), Corynebacterium sp. N-774 (FERM P-4446), etc.
(27) The genus Brevibacterium: *Brevibacterium imperiale* B-222 (FERM P-2721), Brevibacterium sp. R312 (FERM P-2722), Brevibacterium sp. C211 (FERM P-2723), etc.
(28) The genus Nocardia: Nocardia sp. N-775 (FERM P-4447), etc.
(29) The genus Rhodococcus: *Rhodococcus rhodochrous* ATCC 33278, *Rhodococcus rhodochrous* J-1 (FERM BP-1478), *Rhodococcus rhodochrous* IFM 153, *Rhodococcus erythropolis* IFO 12320, *Rhodococcus erythropolis* IFM 155, *Rhodococcus erythropolis* AK 3132 (FERM BP-1040), Rhodococcus sp. s-6 (FERM BP-687), Rhodococcus sp. AK 33 (FERM BP-1047), *Rhodococcus rubropertinctus* JCM 3204, etc.
(30) The genus Arthrobacter: Arthrobacter sp. HR1 (FERM P-11301), *Arthrobacter globisformis* IFO 12138, *Arthrobacter aurescens* IAM 12340, etc.

(36) The genus Agrobacterium: *Agrobacterium radiobacter* SC-C15-1 (FERM BP-3843), etc.
(37) The genus Aspergillus: *Aspergillus nigar* JCM 1925, 2261, etc.
(38) The genus Penicillium: *Penicilliun crysogenum* IFO 5473, etc.
(39) The genus Cochliobolus: *Cochliobolus miyabeanus* OUT 2074, etc.
(40) The genus Fusarium: Fusarium sp. MY-3 (FERM P-9188), etc.
(41) The genus Enterobacter: Enterobacter sp. MC12707 (FERM P-12801), etc.
(42) The genus Xanthobacter: *Xanthobacter flavus* JCM 1204, etc.
(43) The genus Erwinia: *Erwinia nigrifluens* MAFF03-01435, etc.
(44) The genus Citrobacter: *Citrobacter freundii* MC12615 (FERM P-12390), etc.
(45) The genus Aeromonas: Aeromonas sp. MC12615 (FERM P-12390), etc.
(46) The genus Gordona: *Gordona rubropertinctus* JCM 3204, etc.

The microorganisms with IFO numbers for accession are available from Institute for Fermentation, Osaka (IFO), the microorganisms with ATCC numbers from American Type Culture Collection (ATCC), the microorganisms with IAM numbers from IAM Culture Collection, Institute of Applied Microbiology, The University of Tokyo, the microorganisms with IFM numbers from Research Center for Pathogenic Fungi and Toxicoses, Chiba University (IFM), and the microorganisms with JCM numbers from Japan Collection of Microorganisms, The Institute for Physical and Chemical Research. The microorganisms with FERM numbers have been deposited with the National Institute of Bioscience and Human-Technology (or, Fermentation Research Institute), Agency of Industrial Science and Technology.

At least one strain of microorganism selected from among those microorganisms is employed. In the present invention, those mutants, fusion cells, and recombinants which are derived from the strain of microorganism can also be utilized.

The microorganism is generally cultivated in a culture medium and submitted to reaction with a nitrile. The culture medium is not so critical in type only if the microorganism can grow thereon or therein. As the medium, a fluid medium containing sources of carbon and nitrogen and other nutrients is generally used. The carbon source that can be used includes carbohydrates such as glucose, sucrose, starch, etc.; alcohols such as sorbitol, methanol, ethanol, glycerol, etc.; organic acids such as fumaric acid, citric acid, acetic acid, etc. and their salts; hydrocarbons such as paraffin etc.; and mixtures of such sources. The nitrogen source includes but is not limited to inorganic acid ammonium salts such as ammonium sulfate, ammonium nitrate, etc.; organic acid ammonium salts such as ammonium fumarate etc.; meat extract, yeast extract, urea and other organic or inorganic nitrogenous substances; and mixtures thereof. The medium may be supplemented with inorganic salts such as magnesium chloride, ferric chloride, etc.; trace metal salts; vitamins; and other nutrients generally used in incubation in suitable proportions. Where necessary, the medium may be further supplemented with factors assisting in growth of the microorganism, buffers effective in maintaining the pH of the medium within an optimum range, and factors (inducers) contributory to enhanced productivity of the reaction product amide or carboxylic acid. As the inducer, at least one compound selected from among nitrites and amides can be employed. The preferred inducer includes aliphatic nitriles of about 2 to 8 carbon atoms (particularly $C_{4-6}$), such as isovaleronitrile, isobutyronitrile, etc.; aromatic nitriles of 7 to 11 carbon atoms, such as benzonitrile etc.; aliphatic amides of about 2 to 8 carbon atoms, (particularly $C_{2-6}$), such as acetamide, propionamide, etc.; and aromatic amides of 7 to 11 carbon atoms, such as benzamide. The more preferred inducer includes isovaleronitrile, for instance.

Cultivation of the above-mentioned strain of microorganism is carried out under conditions favoring its growth, for example pH 2 to 12, preferably pH 4 to 10 and a temperature from 5 to 50° C., preferably 20 to 50° C. Although the microorganism can be grown whether aerobically or anaerobically, aerobic culture is preferred. The cultivation time may for example be about 1 to 240 hours, preferably about 5 to 120 hours, and more preferably about 12 to 72 hours.

The above-mentioned preparation derived from a microorganism includes a variety of preparations that can be provided by subjecting the microorganism to various treatments, for example a preparation available upon disruption of cells, freeze-dried cells, and cell extracts, and enzymes or enzyme systems derived therefrom (crude enzymes or purified enzymes), among others. The extracts mentioned above can be obtained by conventional technologies such as sonication, freeze-thaw treatment, lysozyme method, etc. The enzymes can also be provided by per se known technology. For example, the cells harvested by centrifuging the culture broth are rinsed with water or the like, suspended in a buffer solution with a pH controlled within the stable range of the desired enzyme, and disrupted at a low temperature by means of a French press or by sonication. The cell fragments are removed by centrifugation or the like and the supernatant or cell extract is subjected to ammonium sulfate fractionation and dialysis in the convensional manner to provide a crude enzyme solution. This enzyme solution is purified by, for example, column chromatography on Sephadex G-200 or the like stationary phase to provide the objective enzyme in pure form.

The enzyme used in many cases is (a) nitrile hydratase, (b) nitrile hydratase and amidase, or (c) nitrilase. Nitrile hydratase can be purified, for example from Nocardia sp. N-775 which is described in Japanese Patent Publication No. 31914/1987 (JP-B-62-31914). Nitrilase can be obtained from *Rhodococcus rhodochrous* J1 which is described Japanese Patent Application Laid-open No. 251192/1991 (JP-A-3-251192).

The cells or their preparations can be immobilized by conventional techniques such as polyacrylamide gel immobilization and used in the form of immobilized cells or immobilized enzymes.

The following is a typical flow diagram for the production process of the invention in which a compound of the formula RCN (R is as defined hereinbefore) is used as an exemplary nitrile compound and an alkali metal hydroxide as an exemplary base. In the diagram, M represents an alkali metal.

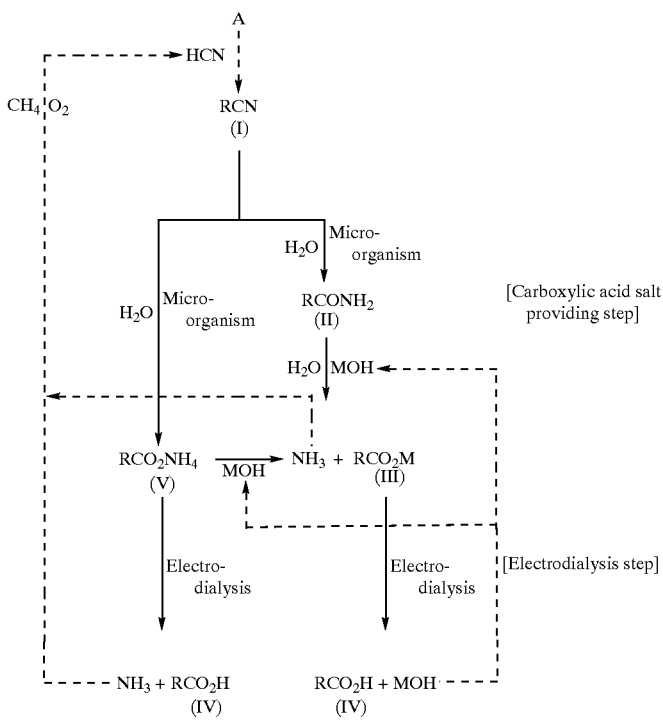

Figure 2:
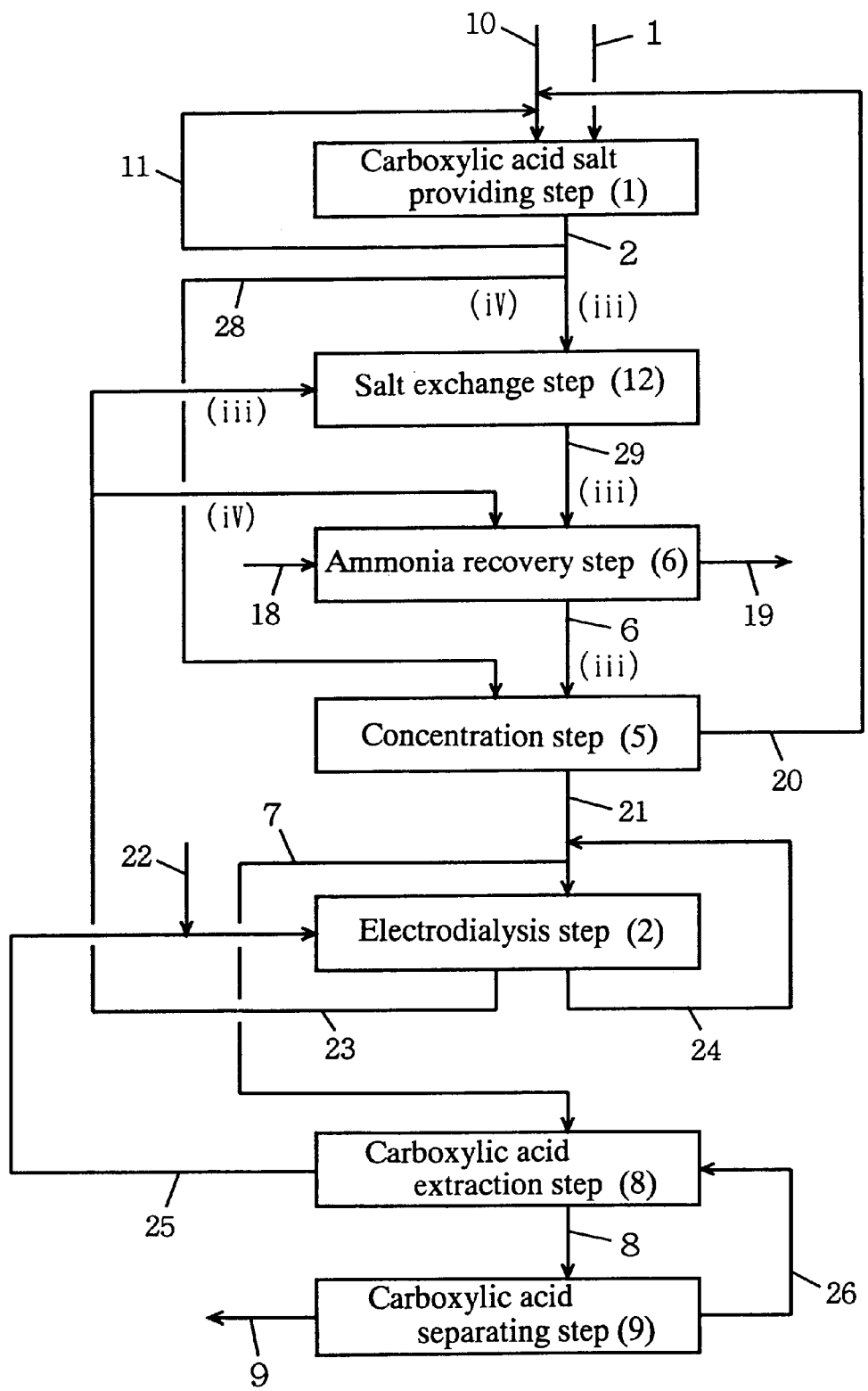
FIG. 2 is a flow diagram of another example of carboxylic acid production technology according to the invention.

FIG. 1 is a flow chart showing an example of the process of the invention and FIG. 2 is a flow chart showing another example of the process of the invention.

In accordance with the present invention, the objective carboxylic acid can be produced by, roughly classified, four different routes, i.e. route (i), route (ii), route (iii), or route (iv), according to the species and strain of microorganism or type of its preparation which is to be permitted to act upon the substrate nitrile. Each of these routes is now described with reference to the flow chart, FIG. 1 [routes (i) and (ii)] or FIG. 2 [routes (iii) and (iv)]. In FIGS. 1 and 2, any line without the designation of (i) to (iv) is a line common to routes (i) and (ii) or to routes (iii) and (iv).

[Route (i)]

Route (i) is suited for the case in which an amide compound is predominantly produced when the strain of microorganism or the preparation derived therefrom is permitted to act upon a nitrile.

Hydration step

In the hydration step, the strain of microorganism or the preparation derived therefrom is permitted to act upon a nitrile of the formula RCN (I) (R is as defined hereinbefore) to produce the corresponding amide (II). Unlike the reaction catalyzed by sulfuric acid, this step using a microorganism or equivalent does not yield reaction byproducts of the nitrile. Therefore, it is no longer necessary to dispose of byproducts which amount to a substantial quantity, nor is a complicated catalyst regeneration procedure required.

Referring to the case illustrated in FIG. 1 and its hydration step (1A), a reactor is charged with the substrate nitrile from a nitrile feed line 1 and water from a water feed line 10 and the hydration reaction is carried out in the presence of the strain of microorganism or the preparation derived therefrom. It should be understood that the reactor may be supplied with the aqueous phase or layer separated in an amide extraction step (4) to be described hereinafter through a water recycle line 13.

The quantity of water used in hydration step (1A) may for example be not less than 0.5 mole (e.g. about 0.5 to 300 moles), preferably not less than 1 mole (e.g. about 1 to 150 moles), per mole of the nitrile. For enhanced solubility of the nitrile and uninterrupted and efficient reaction, the reaction system may be supplemented with an organic solvent, e.g. an ester such as ethyl acetate; a hydrocarbon such as n-hexane; a ketone such as acetone; an alcohol such as methanol, ethanol, etc.; an ether such as dimethoxyethane, tetrahydrofuran, dioxane, etc., among other solvents. A buffer may be employed likewise.

The concentration of the microorganism (cells) or the preparation derived therefrom may for example be about 0.01 to 70 weight %, preferably about 0.1 to 30 weight %. The concentration of the substrate nitrile may for example be about 0.01 to 80 weight %, preferably about 0.05 to 50 weight %, and more preferably about 0.1 to 20 weight %. The pH of the reaction system may for example be pH about 3 to 12, preferably pH about 6 to 10. The reaction time may for example be about 5 minutes to 100 hours.

The mode of reaction may be whichever of the stationary-bed type and the fluidized-bed type, or whichever of the batchwise type and the continuous type. For increased product concentration, the reaction product mixture may be recycled to the reaction system via a reaction mixture recycle line 11.

The reaction mixture is generally transferred to the next step after removal of the microbial cells or equivalent such as preparations derived therefrom by a conventional technique such as centrifugation or filtration.

Amide extraction step

The reaction mixture containing the amide (II) formed in the hydration step is optionally transferred to an amide extraction step, where the amide is extracted into an organic solvent.

Referring to the example illustrated in FIG. 1 and its amide extraction step (4), the reaction mixture containing the amide (II) formed in hydration step (1A) is transferred to an extractor via a hydration reaction mixture feed line 2 and extracted with an organic solvent fed from an organic solvent feed line 14. As the organic solvent, the organic phase or layer separated in an aqueous phase (or layer) separation step (13) to be described below can be utilized. The resulting amide-containing organic layer is fed to hydrolysis step (1B) through an amide-containing mixture feed line 3, while the aqueous phase or layer is recycled to hydration step (1A) through a water recycle line 13.

The organic solvent includes the conventional hydrophobic organic solvents, such as alcohol, ketone, aldehyde, ester, ether, hydrocarbon, or halogenated hydrocarbon series.

The above-mentioned alcohol includes aliphatic alcohols each containing 4 or more carbon atoms, alicyclic alcohols each containing 4 or more carbon atoms, and aromatic alcohols each containing 7 or more carbon atoms. The aliphatic alcohol containing 4 or more carbon atoms includes aliphatic alcohols each containing 4 to about 12 (preferably 4 to about 9) carbon atoms, e.g. $C_4$ alcohols such as 1-butanol, 2-butanol, isobutyl alcohol, etc., $C_5$ alcohols such as 1-pentanol, isoamyl alcohol, tert-amyl alcohol, 2-pentanol, etc., $C_6$ alcohols such as 1-hexanol, 2-methyl-1-pentanol, 3-methyl-1-pentanol, 2,2-dimethyl-1-butanol, 2-ethyl-1-butanol, 4-ethyl-1-pentanol, 2-hexanol, 3-hexanol, 3-methyl-2-pentanol, 2,3-dimethyl-2-butanol, 2-methyl-3-pentanol, 3-methyl-3-pentanol, 4-methyl-2-pentanol, 2-methyl-2-pentanol, etc., $C_7$ alcohol such as n-heptyl alcohol, 2-methyl-1-hexyl alcohol, 3-methyl-1-hexyl alcohol, 4-methyl-1-hexyl alcohol, 5-methyl-1-hexyl alcohol, 2-ethyl-1-pentanol, 3-ethyl-1-pentanol, 2,2-dimethyl-1-pentanol, 3,3-dimethyl-1-pentanol, 4,4-dimethyl-1-pentanol, 2,3-dimethyl-1-pentanol, 2,4-dimethyl-1-pentanol, 3,4-dimethyl-1-pentanol, etc., $C_8$ alcohols such as 1-octanol, 2-methyl-1-heptanol, 3-methyl-1-heptanol, 4-methyl-1-heptanol, 5-methyl-1-heptanol, 2-octanol, 3-octanol, 4-octanol, 2-methyl-2-heptanol, 3-methyl-2-heptanol, 4-methyl-2-heptanol, 5-methyl-2-heptanol, 6-methyl-2-heptanol, 2-methyl-3-heptanol, 3-methyl-3-heptanol, etc., and $C_9$ alcohols such as 1-nonanol etc., among other alcohols.

The alicyclic alcohol of 4 or more carbon atoms includes alicyclic alcohols each containing 4 to about 12 carbon atoms, for example cyclopentanol, cyclohexanol, and cyclooctanol. The aromatic alcohol of 7 or more carbon atoms includes aromatic alcohols each containing 7 to about 12 carbon atoms, such as benzyl alcohol.

The ketone mentioned above includes, for example, ketones each containing 4 or more carbon atoms (e.g. $C_{4-12}$, preferably $C_{4-9}$, approx.), such as methyl ethyl ketone, diethyl ketone, methyl propyl ketone, methyl isopropyl ketone, methyl butyl ketone, methyl 1-methylpropyl ketone, methyl 2-methylpropyl ketone, ethyl propyl ketone, etc.

The aldehyde mentioned above includes, for example, aldehydes of 4 or more carbon atoms (e.g. $C_{4-12}$, preferably $C_{4-9}$, approx.), such as butyraldehyde, valeraldehyde, benzaldehyde, etc.

The ester includes esters of 2 or more carbon atoms (e.g. $C_{2-12}$, preferably $C_{2-9}$, approx.), such as ethyl acetate, propyl acetate, isopropyl acetate, butyl acetate, pentyl acetate, methyl propionate, ethyl propionate, ethyl butyrate, ethyl valerate, etc.

The ether includes but is not limited to ethers of 4 or more carbon atoms (e.g. $C_{4-12}$, preferably $C_{4-9}$, approx.), such as ethyl ether, propyl ether, isopropyl ether, butyl ether, isobutyl ether, etc.

The hydrocarbon includes aliphatic hydrocarbons such as pentane, hexane, heptane, octane, etc.; alicyclic hydrocarbons such as cyclopentane, cyclohexane, etc.; and aromatic hydrocarbons such as benzene, toluene, xylene, ethylbenzene, etc. The halogenated hydrocarbon includes, for example, methylene chloride, chloroform, carbon tetrachloride, dichloroethylene, and chlorobenzene. Those organic solvents can be used independently or in a suitable combination.

The preferred organic solvent includes alcohols, ketones, aldehydes, esters, and ethers. The still more preferred organic solvent includes alcohols or ketones of 4 or more carbon atoms (e.g. $C_{4-12}$, approx.).

The organic solvent which can be used for extraction includes not only the organic phase or layer provided in the aqueous phase or layer separating step (13) but also the organic solvent provided in the carboxylic acid separating step (9) described below in detail, as well as a fresh organic solvent.

The extraction can be carried out by a conventional procedure, for example by adding an organic solvent to the reaction mixture available from the hydration step (1A) and stirring or shaking the mixture. The extraction can be carried out batchwise or continuously.

The organic phase or layer containing the amide (II) formed in amide extraction step (4) is transferred, either as it is or after adjustment to a suitable concentration, to the hydrolysis step (1B). Even when the amide compound (II) and the organic solvent are fed together to hydrolysis step (1B), the carboxylic acid salt formed by hydrolysis transfers into the aqueous phase or layer so that the organic solvent and the salt can be easily separated from each other. Moreover, when the hydrolysis is carried out in the presence of such an organic solvent, the reaction proceeds smoothly so that, in many instances, the carboxylic acid salt can be obtained in good yield. Thus, although the amide may be isolated from the organic phase or layer beforehand and fed to hydrolysis step (1B), the organic phase or layer containing the amide may be directly transferred to hydrolysis step (1B).

The aqueous phase or layer provided in the amide extraction step (4) can be reutilized by recycling it to hydration step (1A). This aqueous phase or layer may also be recycled to hydrolysis step (1B) or electrodialysis step (2) as will be described hereinafter. Moreover, the aqueous phase or layer may be discarded. Even if it is discarded, the aqueous phase or layer not containing byproducts such as ammonium hydrogen sulfate does not play havoc of the environment unlike the case of using sulfuric acid as a catalyst.

Where the reaction mixture available in the hydration step (1A) contains not only the amide but also the corresponding carboxylic acid salt [ammonium salt (V)], the extraction results in the transfer of the carboxylic acid salt to the aqueous phase or layer in many instances. In such cases, the carboxylic acid can be recovered from the aqueous phase or layer by treating the phase or layer in the same way as the reaction mixture from carboxylic acid salt providing step (1) in route (iii) which will hereinafter be described in detail.

The reaction mixture obtained in hydration step (1A) can be fed to hydrolysis step (1B) bypassing amide extraction step (4).

Hydrolysis step

In the hydrolysis step, the amide (II) formed in the hydration step is hydrolyzed in the presence of a base to give the salt (III) of the corresponding carboxylic acid with the base as well as ammonia. When the carboxylic acid salt [ammonium salt (V)] is present in the feed to the hydrolysis step, a salt exchange reaction may take place. For example, when a base with higher basicity than ammonia, such as an alkali metal hydroxide, is used as the base, the ammonium carboxylate is converted to the salt corresponding to the base used, such as the alkali metal salt of the carboxylic acid, with liberation of ammonia.

In this step, which uses a base as a hydrolysis catalyst, unlike the use of sulfuric acid as a catalyst, the nitrogen atom of the amide compound and, hence, the nitrogen atom of the nitrile compound can be recovered in the form of ammonia.

In the example illustrated in FIG. 1, the reactor in the hydrolysis step (1B) is charged with the amide compound from an amide-containing mixture feed line 3 and the base and water from a base-water feed line 15 for effecting the hydrolysis reaction.

The base may be whichever of an inorganic base or an organic base. The inorganic base includes, for example, alkali metal hydroxides such as lithium hydroxide, sodium hydroxide, potassium hydroxide, rubidium hydroxide, cesium hydroxide, etc.; alkali metal carbonates such as sodium carbonate, potassium carbonate, etc.; alkali metal hydrogen carbonates such as sodium hydrogen carbonate, potassium hydrogen carbonate, etc.; alkaline earth metal hydroxides such as magnesium hydroxide, potassium hydroxide, etc.; and alkaline earth metal carbonates such as magnesium carbonate, potassium carbonate, etc.

The organic base includes mono-, di-, or trialkylamines such as triethylamine, tripropylamine, tributylamine, etc.; cyclic amines such as piperazine, piperidine, N-methylpiperidine, morpholine, etc.; alkanolamines such as ethanolamine, triethanolamine, etc.; and basic nitrogen-containing heterocyclic compounds such as pyridine. The electrodialysis step (2) in which the carboxylic acid salt formed in hydrolysis step (1B) is decomposed into the carboxylic acid and the base is conducted in the presence of water. Therefore, the base is preferably a water-soluble compound.

The preferred base includes alkali metal hydroxides (sodium hydroxide, potassium hydroxide, etc.) and alkali metal carbonates (sodium carbonate, potassium carbonate, etc.). The still more preferred base includes sodium hydroxide and potassium hydroxide.

The base can be used singly or as a mixture of two or more species. For an increased reaction rate, the pKa of the base may, for example, be not less than 6 (e.g. about 6 to 30), preferably not less than 9 (e.g. about 9 to 20), and more preferably about 14 to 18.

The proportion of the base relative to one mole of the amide compound may for example be not less than 0.5 gram equivalent, preferably 1 to 5 gram equivalents. If the proportion of the base is less than 0.5 gram equivalent, much of the amide compound will remain unreacted, thus complicating the recovery procedure in some instances. Use of the base in a proportion of over 5 gram equivalents will be uneconomical.

The concentration of the base in the reaction system may for example be not less than 0.1 normal (e.g. about 0.1 to 5 N), preferably 0.2 to 3 N (e.g. about 0.5 to 3 N). If the concentration of the base is less than 0.1 N, not only will the reaction be retarded but the volume of reaction system necessary to obtain a given output (quantity) of the carboxylic acid will be increased to adversely affect productivity.

In hydrolysis step (1B), water is generally used in stoichiometric excess over the amide compound. Thus, the amount of water may for example be not less than 1 mole (e.g. about 1 to 500 moles), preferably not less than 1.5 moles (e.g. about 1.5 to 300 moles), per mole of the amide.

The reaction temperature is generally about 20 to 150° C. and preferably about 30 to 120° C. If the reaction temperature is below 20° C., the reaction will tend to be retarded. If it exceeds 150° C., side reactions will take place to depress the yield of the objective product. The reaction pressure need only be high enough to maintain the reaction system in liquid phase at the reaction temperature, and may for example be 1 to 20 atmospheres, preferably 1 to 10 atm., although the reaction is carried out at atmospheric pressure in many cases. The reaction time depends on the other reaction conditions such as the species and quantity of the base used, the reaction temperature, etc. and cannot be specified in general terms but it is generally about 0.1 to 10 hours. The reaction can be carried out batchwise or continuously.

Thus, starting with a nitrile (I), the corresponding carboxylic acid salt can be produced by carrying the nitrile (I) serially through hydration step (1A) and hydrolysis step (1B).

As the base and water needed for the hydrolysis reaction, the base and water recovered in the electrodialysis step (2) and/or carboxylic acid extraction step (8), to be described hereinafter, can be reused with efficiency, although the whole or part of the respective requirements may be supplied afresh.

Aqueous layer separating step

The reaction mixture obtained in the hydrolysis step is optionally fed to the aqueous layer separating step. Separation of an aqueous layer can be effected by subjecting the reaction mixture obtained in the hydrolysis step to phase separation into an organic layer and an aqueous layer. This step is useful when the reaction mixture obtained in the hydrolysis step contains an organic solvent. For example, when the amide compound is fed together with the organic solvent used as an extractant in the amide extraction step to the hydrolysis step, the reaction mixture obtainable in the hydrolysis step contains the organic solvent. This organic solvent can be easily recovered in the aqueous layer separating step.

Referring to the example illustrated in FIG. 1 and particularly to the aqueous layer separating step (13), the reaction product mixture from hydrolysis step (1B) is fed to a phase separation equipment through a hydrolyzate mixture feed line 4 and separated into an organic phase or layer containing the organic solvent and an aqueous phase or layer containing the carboxylic acid salt and ammonia.

The organic phase or layer is predominantly composed of the organic solvent and can therefore be recycled through an organic solvent feed line 17 for use as an extraction solvent in the amide extraction step (4). The organic phase or layer can also be used as an extraction solvent in carboxylic acid extraction step (8) which will be described hereinafter in detail. On the other hand, the aqueous phase or layer is fed to ammonia recovery step (6) through a carboxylate-containing mixture feed line 5.

It should be understood that the reaction mixture obtained in hydrolysis step (1B) may be fed to ammonia recovery step (6) or electrodialysis step (2) instead of being fed to aqueous layer separating step (13).

Ammonia recovery step

The aqueous phase or layer obtained in the aqueous layer separating step can be optionally fed to this ammonia recovery step for recovery of ammonia. The recovery of ammonia can be effected by stripping with an inert gas or heating for gasification of dissolved ammonia.

In the ammonia recovery step (6) of the example illustrated in FIG. 1, the ammonia dissolved in the aqueous phase or layer fed from aqueous layer separating step (13) through carboxylate-containing mixture feed line 5 is stripped with an inert gas supplied from an inert gas feed line 18 and the mixture gas comprising the inert gas and ammonia is recovered from an ammonia recovery line 19. The inert gas mentioned above includes gaseous nitrogen, helium, argon, methane, carbon dioxide, and carbon monoxide, among other gases. The recovery of ammonia can be carried out batchwise or continuously.

The recovered ammonia can be used as a reactant in the production of cyanogen compounds such as hydrogen cyanide which is a starting material for nitriles. Thus, the ammonia can be reused as a nitrogen source for nitrile compounds. For example, hydrogen cyanide can be produced from ammonia, methanol and carbon monoxide in accordance with the following reaction formula (c).

$$CH_3OH + CO \rightarrow HCOOCH_3 \quad HCOOCH_3 + NH_3 \rightarrow HCONH_2 + H_2O$$
$$HCONH_2 \rightarrow HCN + H_2O \quad (c)$$

Furthermore, starting with ammonia, methane, and oxygen, hydrogen cyanide can be produced according to the following reaction formula (d).

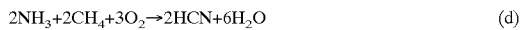

$$2NH_3 + 2CH_4 + 3O_2 \rightarrow 2HCN + 6H_2O \quad (d)$$

The nitrile (I) can be easily produced by subjecting the hydrogen cyanide to reaction with a mating starting compound A (e.g. a ketone, an aldehyde, or an epoxide).

When, in the ammonia recovery step (6), the ammonia is stripped using methane as the inert gas, the resulting mixture gas comprising methane and ammonia can be fed to the hydrogen cyanide production line designated as (d) above so that the ammonia can be recycled and reused with high efficiency and convenience.

It should be understood that the aqueous layer separating step (13) and the ammonia recovery step (6) can be carried out in a reversed order. Thus, it is possible to feed the hydrolyzate mixture from hydrolysis step (1B) to ammonia recovery step (6) for recovery of ammonia by stripping or the like and then feed the carboxylate-containing mixture after recovery of ammonia to the aqueous layer separating step (13) so as to separate it into an organic layer containing the organic solvent and an aqueous layer containing the carboxylate. In this instance, the organic layer can be recycled to the amide extraction step (4), for instance, while the aqueous layer can be fed to electrodialysis step (2), optionally after concentration in concentration step (5).

The ammonia formed in hydrolysis step (1B) need not necessarily be recovered but the reaction mixture in hydrolysis step (1B) may be first fed to aqueous layer separating step (13) or concentration step (5) as necessary and then fed to electrodialysis step (2).

Concentration step

The mixture obtained in the ammonia recovery step may be transferred to this concentration step as necessary to increase the concentration of the carboxylic acid salt and, hence, the efficiency of dialysis in the electrodialysis step.

Referring to the example illustrated in FIG. 1 and particularly to concentration step (5), the mixture containing the carboxylic acid salt after recovery of ammonia is fed to a concentration equipment through a carboxylate-containing mixture feed line 6. The concentration can be conducted in accordance with a conventional manner. This concentration step and the ammonia recovery step can be carried out using the same equipment. The degree of concentration is not critical but may be within limits not causing precipitation of the carboxylate to interfere with electrodialysis. Generally, concentration is carried out until the carboxylate concentration will be about 0.1 to 5 normal.

The concentrate is fed to electrodialysis step (2) through a carboxylate-containing mixture feed line 21. The distillate water can be reused in hydration step (1A) or hydrolysis step (1B). The concentration step (5) and ammonia recovery step (6) can be carried out in a reverse order.

In the process of the invention including the amide extraction step (4) for extracting the amide from the reaction mixture obtained in hydration step (1A), the amide concentration of the amide-containing mixture can be increased so that the carboxylate concentration in the feed to the electrodialysis step can also be held high. In this embodiment, therefore, the current efficiency of electrodialysis step (2) can be improved even if the concentration step (5) is omitted.

Electrodialysis step

In the electrodialysis step, the carboxylic acid salt (III) formed in the hydrolysis step is subjected to electrodialysis to provide the corresponding carboxylic acid (IV) and base.

The electrodialysis according to the present invention is principally equivalent to the hydrolysis described in Ion Exchange Membranes, Yujiro Kosaka & Hiroshi Shimizu (ed.), page 233 (Kyoritsu Shuppan, Co., Ltd., Japan). The electrodialyzer comprises a bipolar membrane and at least one membrane selected from among cation exchange membranes and anion exchange membranes. The electrodialysis cell configuration is not critical but the conventional two-compartment or three-compartment electrodialyzer can for example be employed.

The two-compartment electrodialyzer comprises a bipolar membrane and either a cation exchange membrane or an anion exchange membrane as disposed between bipolar membrane components. The anion exchange membrane side of the bipolar membrane is disposed in face-to-face relation to the positive electrode and the cation exchange membrane side is disposed in face-to-face relation to the negative electrode. As a voltage is applied across the two electrodes, the water molecule reaching the interface between the anion exchange membrane and cation exchange membrane sides of the bipolar membrane is decomposed to yield $H^+$ ion on the anion exchange membrane side and $OH^-$ ion on the cation exchange membrane side.

There is no particular limitation on the cation exchange membrane that can be used, and there can be used conventional cation exchange membranes, for example a cation exchange membrane having cation exchange groups such as sulfonic, carboxyl, phosphonic, sulfate, or phosphate groups. There is no particular limitation on the anion exchange membrane, either, and there can be used the conventional anion exchange membranes, for example an anion exchange membrane having anion exchange groups such as primary amino, secondary amino, tertiary amino, or quaternary amino groups.

There is no particular limitation on the bipolar membrane, and any of the conventional bipolar membranes can be employed. For example, a bipolar membrane can be fabricated by laminating a cation exchange membrane to an anion exchange membrane with a polyethylene-epichlorohydrin mixture. It can also be fabricated by depositing a sulfonic acid-series polymeric electrolyte and allylamine, for instance, on the surface of an anion exchange membrane and irradiating the whole with an electrolytic or active radiation.

The concentration of the carboxylic acid salt in the mixture to be electrically dialyzed is generally about 0.1 to 5 normal. This electrodialysis can be carried out batchwise or continuously.

Referring to the example illustrated in FIG. 1 and particularly to electrodialysis step (2), an electrodialysis cell equipped with ion exchange membranes is charged with a mixture containing the carboxylate (III) and water as obtained in hydrolysis step (1B) from a carboxylate-containing mixture feed line 21 and water from a water feed line 22 for electrodialysis.

In this electrodialysis step (2), the corresponding carboxylic acid (IV) and base are produced from the carboxylate (III), and as a consequence a mixture containing the carboxylic acid (IV) and water and a mixture containing the base and water are independently obtained. The mixture containing the product carboxylic acid (IV) and water, through a carboxylic acid-containing mixture recycle line 24, is mixed with the mixture containing the carboxylate (III) and water from the carboxylate-containing mixture feed line 21 and the whole mixture is recycled to electrodialysis step (2). It should be understood that depending on conditions of electrodialysis, the mixture containing carboxylate (IV) and water contains undecomposed carboxylate (III).

On the other hand, the mixture containing the base and water as formed in the electrodialysis step can be recovered from a base-water recovery line 23. The recovered base can be recycled to hydrolysis step (1B) for reuse as the catalyst.

A portion of the feed (the mixed feed from the carboxylate-containing mixture feed line 21 and the carboxylic acid-containing mixture recycle line 24) to electrodialysis step (2) is fed to carboxylic acid extraction step (8) through a carboxylic acid-containing mixture feed line 7. It should be understood that the mixture containing the carboxylic acid (IV) formed in electrodialysis step (2) and water can be directly fed to carboxylic acid extraction step (8) without being recycled to electrodialysis step (2).

Carboxylic acid extraction step and carboxylic acid separating step

Where necessary, the carboxylic acid produced in the electrodialysis step can be subjected to carboxylic acid extraction and carboxylic acid separating steps for recovery.

Referring to the example illustrated in FIG. 1 and particularly to carboxylic acid extraction step (8), the mixture containing the carboxylic acid (IV) and water as formed in electrodialysis step (2) is fed to an extractor from a carboxylic acid-containing mixture feed line 7 and the carboxylic acid (IV) is extracted into an organic solvent supplied from an organic solvent feed line 26.

The organic solvent that can be used includes the organic solvents mentioned for the amide extraction step (4), such as alcohols, ketones, aldehydes, esters, and ethers. The preferred organic solvent includes alcohols and ketones each containing 4 or more carbon atoms (e.g. about 4 to 12 carbon atoms). Extraction can be carried out by the conventional procedure.

The organic phase or layer containing the carboxylic acid (IV) and organic solvent is fed to carboxylic acid separating step (9) through a carboxylic acid extract feed line 8. On the other hand, the aqueous phase or layer can be withdrawn from water recovery line 25 and recycled, together with the base-containing aqueous mixture from base-water recovery line 23, to electrodialysis step (2) via water feed line 27 or recycled to hydrolysis step (1B) via a base-water feed line 15.

In carboxylic acid separating step (9), the organic layer containing the carboxylic acid (IV) and organic solvent as available from the carboxylic acid extraction step (8) is distilled to separate the carboxylic acid (IV) from the organic solvent. The carboxylic acid (IV) is recovered from a carboxylic acid recovery line 9, while the organic solvent can be recycled to carboxylic acid extraction step (8) through an organic solvent feed line 26 for reuse as the extraction solvent. The recovered organic solvent may also be used as the extraction solvent in amide extraction step (4).

The extraction of carboxylic acid (IV) and the separation of carboxylic acid (IV) can respectively be carried out batchwise or continuously.

It should be understood that the carboxylic acid (IV) formed in electrodialysis step (2) can be separated and recovered from the mixture containing carboxylic acid (IV) and water not only by the above method but also by the conventional procedure, for example extraction, distillation, crystallization, recrystallization, column chromatography, etc., or any suitable combination of such procedures.

[Route (ii)]

Route (ii) corresponds to route (i) from which the amide extraction step (4) and aqueous layer separating step (13) have been omitted. Route (ii) is suitable for the case in which permitting the strain of microorganism or the preparation derived therefrom to act upon a nitrite results in formation of a mixture of the amide compound and carboxylic acid salt.

In the example illustrated in FIG. 1, the reaction mixture obtained in hydration step (1A) is fed to hydrolysis step (1B) through a hydration reaction mixture feed line 12 and the reaction mixture provided in hydrolysis step (1B) is fed to ammonia recovery step (6) through a hydrolysis reaction mixture feed line 16.

In hydrolysis step (1B), the amide (II) in the reaction mixture obtained in hydration step (1A) is hydrolyzed with a base to the corresponding carboxylic acid salt (III) and ammonia, while the ammonium carboxylate (V) in the reaction mixture undergoes salt exchange reaction with the base to give the corresponding carboxylic acid salt (III) and ammonia.

According to this route (ii) bypassing amide extraction step (4), any ammonium carboxylate (V) in the reaction mixture obtained in hydration step (1A) is not lost through transfer to the aqueous phase or layer. Moreover, the omission of amide extraction step (4) and aqueous layer separating step (13) results in simplification of the process. In addition, since many strains of microorganism capable of hydrating nitrites have both the enzyme converting nitrites to amides and the enzyme converting nitrites to carboxylic acids, this route (ii) is compatible with a broad spectrum of microorganisms and, therefore, can be more universally employed.

[Route (iii)]

Route (iii) is suitable for the case in which permitting the strain of microorganism or the preparation derived therefrom to act upon a nitrile results predominantly in production of the corresponding carboxylic acid salt.

Carboxylic acid salt providing step

In the carboxylic acid salt providing step, the strain of microorganism or the preparation derived therefrom is permitted to act upon a nitrile to provide the corresponding ammonium carboxylate (V).

Referring to the example illustrated in FIG. 2 and particularly to carboxylic acid salt providing step (1), a reactor is supplied with the nitrile from a nitrile feed line 1 and water from a water feed line 10 and the hydration reaction is conducted in the presence of the strain of microorganism capable of converting nitriles to carboxylic acids or the preparation derived therefrom. It should be understood that the reactor may be supplied with the distillate water available in a concentration step (5) to be described hereinafter through a water recycle line 20.

The amount of water to be used in this carboxylic acid salt providing step (1) may for example be not less than 1.5 moles (e.g. about 1.5 to 300 moles), preferably not less than 2 moles (e.g. about 2 to 150 moles), per mole of the nitrile. For improved solubility of the nitrile and smooth progress of the reaction, an organic solvent such as those mentioned for route (i) may be added to the reaction s yste m. A buffer may also be used.

The concentration of the strain of microorganism (cells) or preparation, the concentration of the nitrile, the reaction system pH, and the reaction time can be the same as those mentioned for the hydration step (1A) in route (i). The mode of reaction may be a stationary-bed reaction or a fluidized-bed reaction, and may be batchwise or continuous. For enhanced concentration of the reaction product, the reaction mixture may be recycled to the reaction system via a reaction mixture recycle line 11.

The reaction mixture is generally subjected to a conventional separating procedure, such as centrifugation or filtration, to remove the microbial cells or the preparation derived from the microorganism before being fed to the next step.

Salt exchange step

In the salt exchange step, a base is permitted to act upon the ammonium carboxylate (V) formed in the carboxylic acid salt providing step for salt exchange to provide the corresponding carboxylic acid salt (III) and ammonia.

Referring to the example illustrated in FIG. 2 and, in particular, to salt exchange step (12), the reaction mixture containing ammonium carboxylate (V) as obtained in the carboxylic acid salt providing step is fed to a salt-exchange reactor through a hydration product-containing mixture feed line 2, while a base is fed to the reactor from a base feed line 14.

The base that can be used in this step includes the bases mentioned for the hydrolysis step (1B) in route (i). The preferred base includes alkali metal hydroxides (sodium hydroxide, potassium hydroxide, etc.) and alkali metal carbonates (sodium carbonate, potassium carbonate, etc.). The still more preferred base includes sodium hydroxide and potassium hydroxide. Those bases can be used independently or in a combination of two or more species.

The amount of the base per mole of ammonium carboxylate (V) may for example be not less than 0.5 gram equivalent, preferably about 1 to 5 gram equivalents, and more preferably about 1 to 2 (particularly 1 to 1.5) gram equivalents. The salt exchange reaction can be conducted in a temperature range of about 0° C. to 50° C. but is generally carried out at room temperature. The reaction may be carried out batchwise or continuously.

It should be understood that by permitting the strain of microorganism or the preparation derived therefrom to act upon the nitrile in the carboxylic acid salt providing step (1), both the hydration of the nitrile and the salt exchange reaction can be carried out in one step.

This salt exchange step converts the ammonium carboxylate to, for example an alkali metal salt which has a higher current efficiency for electrodialysis. By utilizing this step, the efficiency of carboxylic acid production can be remarkably improved.

Ammonia recovery step

In this ammonia recovery step, the ammonia produced in the salt exchange step is recovered. This recovery of ammonia can be carried out in the same manner as in the route (i).

Referring to the example illustrated in FIG. 2 and, in particular, to ammonia recovery step (6), the reaction mixture available from salt exchange step (12) is fed to an ammonia recovery equipment through a salt-exchange product-containing mixture feed line 29 and stripped with an inert gas supplied from an inert gas feed line 18, and the resulting mixture of the inert gas with ammonia gas is recovered from an ammonia recovery line 19. As the inert gas mentioned above, the gases mentioned hereinbefore can be employed. The recovery of ammonia may be batchwise or continuous.

The recovered ammonia can be used as a reactant for the synthesis of cyanogen compounds such as hydrogen cyanide which is used as a starting material for nitriles.

Thus, a nitrile (I) can be easily produced by subjecting the hydrogen cyanide to reaction with another starting compound A (e.g. a ketone, aldehyde, or epoxide).

Concentration step

The mixture obtained in the ammonia recovery step can be fed to a concentration step as necessary to increase the concentration of the carboxylic acid salt and, hence, the efficiency of dialysis in the electrodialysis step.

Referring to the example illustrated in FIG. 2 and particularly to concentration step (5), the mixture containing the carboxylic acid salt (III) after recovery of ammonia is fed to a concentration equipment through a carboxylate-containing mixture feed line 6. Concentration can be carried out in the same manner as in route (i). The resulting concentrate is fed to electrodialysis step (2) through a line 21. The distillate water can be fed for reuse to carboxylic acid salt providing step (1) through a line 20.

It should be understood that the concentration step (5) need not necessarily be disposed downstream of ammonia recovery step (6) but can be disposed either upstream or downstream of the salt exchange step (12).

Electrodialysis step. carboxylic acid extraction step, and carboxylic acid separating step The electrodialysis step, carboxylic acid extraction step, and carboxylic acid separating step can be carried out in substantially the same manner as in the route (i). The base available from electrodialysis step (2) can be fed for reuse to the salt exchange step (12) through a base-water recovery line 23.

[Route (iv)]

Route (iv) is also suitable for the case in which permitting the strain of microorganism or the preparation derived therefrom to act upon the nitrile results predominantly in production of the corresponding carboxylate.

Route (iv) is different from route (iii) in that it does not include the salt exchange step (12) and that the ammonia available from the electrodialysis step is recovered in an ammonia recovery step. Route (iv) is advantageous in that the objective carboxylic acid can be produced in a short sequence of Steps. The differences of this route from route (iii) are now explained.

Concentration step

In the concentration step, the reaction mixture available from the carboxylic acid salt providing step is concentrated. In the example illustrated in FIG. 2, the reaction mixture formed in carboxylic acid salt providing step (1) is fed to a concentration equipment through a hydration product mixture feed line 28. Concentration can be carried out in the same manner as described hereinbefore. The concentrate available from concentration step (5) is fed to electrodialysis step (2) through a carboxylate-containing mixture feed line 21. The distillate water available in this concentration step can be reused in carboxylic acid salt providing step (1).

Ammonia recovery step

In the ammonia recovery step, the aqueous ammonia formed in electrodialysis step (2) is fed to an ammonia recovery equipment for recovery in the same manner as described hereinbefore. The recovered ammonia can be used as a starting material in a nitrile production line.

In accordance with the method of the invention which comprises a hydration reaction of a nitrile using a strain of microorganism or a preparation derived therefrom and an electrodialysis of the corresponding carboxylic acid salt in combination, byproducts such as ammonium hydrogen sulfate are not formed. Moreover, the method insures a n expedient recovery of useful ammonia and the catalyst.

Furthermore, the ammonia and catalyst substance can be effectively utilized.

The following examples are intended to describe the present invention in further detail and should by no means be construed as defining the scope of the invention.

EXAMPLES

Example 1

2-Hydroxy-4-methylthiobutanoic acid (α-hydroxy-4-methylthiobutyric acid) was produced in accordance with route (i) in the production flow diagram shown in FIG. 1. In this example, the objective carboxylic acid was produced bypassing the concentration step (5).

Hydration step (1A)

A loopful of *Gordona rubropertinctus* JCM 3204 from a slant culture was used to inoculate 1,000 ml/Sakaguchi flask of the following liquid medium and shake-cultured aerobically at 30° C. for 48 hours.

Medium (unit: w/v)

| | |
|---|---|
| Glycerol | 2% |
| Yeast extract | 0.3% |
| Monopotassium phosphate | 0.5% |
| Dipotassium phosphate | 0.5% |
| Sodium sulfate | 0.1% |
| Magnesium sulfate | 0.05% |
| Calcium chloride | 0.005% |
| Manganese sulfate | $1 \times 10^{-4}\%$ |
| Iron chloride | $1 \times 10^{-5}\%$ |
| Zinc sulfate | $1 \times 10^{-5}\%$ |
| Isovaleronitrile (inducer) | 0.2% |
| pH | 7.2 |

The liquid medium was then centrifuged to harvest the cells, which were then washed 3 times each with a portion of 0.05 M phosphate buffer (pH 7.0). After the washed cells were resuspended in 250 ml of the same buffer as above, 2-hydroxy-4-methylthiobutanenitrile (α-hydroxy-4-methylthiobutyronitrile) was added in a final concentration of 330 mM and allowed to react at 5° C. for 24 hours. After completion of the reaction, the reaction mixture was centrifuged to remove the cells and recover a supernatant. Analysis of the supernatant by liquid chromatography revealed that it contained 4.1 weight % of 2-hydroxy-4-methylthiobutanamide (α-hydroxy-4-methylthiobutyramide) and 0.9 weight %, on a free acid basis, of ammonium 2-hydroxy-4-methylthiobutanoate (ammonium α-hydroxy-4-methylthiobutyrate). The yield of 2-hydroxy-4-methylthiobutanamide was 83% and the yield of ammonium 2-hydroxy-4-methylthiobutanoate was 17%.

Amide extraction step (4)

An extraction column packed with Raschig rings was charged with the reaction mixture obtained in the hydration step (1A) (supernatant) through the hydration reaction mixture feed line 2 at a flow rate of 3,634 g/hr. and, at the same time, with an extraction solvent comprising methyl ethyl ketone and a small proportion of water (the organic layer available in an aqueous layer separating step (13) to be described hereinafter) at a flow rate of 4,600 g/hr.

As a result, an organic layer containing 2-hydroxy-4-methylthiobutanamide and methyl ethyl ketone was obtained at a flow rate of 4,750 g/hr. (149 g/hr. as 2-hydroxy-4-methylthiobutanamide).

Hydrolysis step (1B)

A 5 L-glass reactor equipped with a stirrer was continuously charged with the organic layer obtained in the amide extraction step through an amide mixture feed line 3 and, at the same time, with an 8% aqueous solution of sodium hydroxide containing a small amount of sodium 2-hydroxy-4-methylthiobutanoate (a mixture of the aqueous solution of sodium hydroxide obtained in electrodialysis step (2) with the aqueous layer obtained in carboxylic acid extraction step (8)) from a base-water feed line 15 at a flow rate of 540 g/hr, and the hydrolysis reaction was carried out at: a reaction temperature of 60° C.

As a result, a reaction mixture comprising sodium 2-hydroxy-4-methylthiobutanoate (230 g/hr.), ammonia (17 g/hr.), water, and methyl ethyl ketone was obtained at a flow rate of 1,390 g/hr.

Aqueous layer separating step (13)

The reaction mixture obtained in hydrolysis step (1B) was fed to a phase separation equipment from a hydrolyzate mixture feed line 4. The resulting organic layer (methyl ethyl ketone containing 10% of water) was recycled to amide extraction step (4) through an organic solvent feed line 17 as mentioned above at a flow rate of 690 g/hr.

Ammonia recovery step (6)

An ammonia stripping column packed with Raschig rings was charged with the aqueous phase or layer containing sodium 2-hydroxy-4-methylthiobutanoate and ammonia as obtained in aqueous layer separating step (13) through a carboxylate-containing mixture feed line 5 and, at the same time, with 23 L/hr of methane gas from an inert gas feed line 18 connected to the bottom of the ammonia stripping column.

As a result, a methane-ammonia mixture gas was obtained from the top of the ammonia stripping column. This mixture gas was fed to a prussic acid production line from an ammonia recovery line 19.

Electrodialysis step (2)

An electrodialyzer (TS2B-2-5, effective area 200 cm$^2$×5 pairs, manufactured by Tokuyama Co., Ltd.) comprising a bipolar membrane and a cation exchange membrane (both manufactured by Tokuyarna Co., Ltd.) were used.

This electrodialyzer was charged with a mixture of the aqueous solution of sodium 2-hydroxy-4-methylthiobutanoate from which ammonia had been removed in the ammonia recovery step (6) (carboxylate-containing mixture feed line 6) and the aqueous solution containing 2-hydroxy-4-methylthiobutanoic acid and undecomposed sodium 2-hydroxy-4-methylthiobutanoate as available from the electrodialysis step (carboxylic acid-containing mixture recycle line 24). The concentration of sodium 2-hydroxy-4-methylthiobutanoate in this mixture was 8.8 weight % and the rate of feed to the electrodialyzer was 3,600 g/hr. A portion of the mixture (655 g/hr.) was fed to carboxylic acid extraction step (8).

The aqueous solution of sodium hydroxide available on electrodialysis was mixed with the aqueous layer (an aqueous solution containing undecomposed sodium 2-hydroxy-4-methylthiobutanoate; water recovery line 25) obtained in a carboxylic acid extraction step (8) described below through a base-water recovery line 23, and a portion of the mixture was fed as the electrolyte to the electrodialyzer via a water feed line 27, while the remaining major portion was recycled to hydrolysis step (1B) through a base-weLter feed line 15. On the other hand, water (unused fresh water) was fed to the dialyzer through a water feed line 22 at a flow rate of 18 g/hr.

Carboxylic acid extraction step (8)

An extraction column was charged, via a carboxylic acid mixture feed line 7, with a mixture of the aqueous solution of sodium 2-hydroxy-4-methylthiobutanoate from which ammonia had been removed in the ammonia recovery step (6) (line 6) and the carboxylic acid-containing mixture (an aqueous solution containing 2-hydroxy-4-methylthiobutanoic acid and undecomposed sodium 2-hydroxy-4-methylthiobutanoate) from carboxylic acid mixture recycle line 24. At the same time, methyl ethyl ketone was fed as the extraction solvent from an organic solvent feed line 26.

As a result, an extract (organic layer) containing 18.5 weight % of 2-hydroxy-4-methylthiobutanoic acid, 73 weight % of methyl ethyl ketone, and 8.5 weight % of water was obtained at a flow rate of 805 g/hr. As mentioned hereinbefore, the aqueous layer containing undecomposed sodium 2-hydroxy-4-methylthiobutanoate was recycled, together with the aqueous solution of sodium hydroxide in base-water recycle line 23, to hydrolysis step (1B) and electrodialysis step (2) through a water recovery line 25.

Carboxylic acid separating step (9)

The extract (organic layer) obtained in carboxylic acid extraction step (8) was fed through a carboxylic acid extract feed line 8 to a distillation column for distillation. As a result, an aqueous solution containing 80% of 2-hydroxy-4-methylthiobutanoic acid and having a Gardner color scale number of 4 was obtained from the bottom of the column through a carboxylic acid recovery line 9 at a flow rate of 178 g/hr. On the other hand, the methyl ethyl ketone fraction available from the column top was recycled to the carboxylic acid extraction step (8) from an organic solvent feed line 26 for reuse as the extraction solvent.

Example 2

2-Hydroxy-4-methylthiobutanoic acid was produced in accordance with route (ii) in the production flow illustrated in FIG. 1.

Hydration step (1A)

The procedure described in Example 1 was repeated to provide a reaction mixture containing 4.1 weight % of 2-hydroxy-4-methylthiobutanamide and 0.9 weight % of ammonium 2-hydroxy-4-methylthiobutanoate.

Hydrolysis step (1B)

A 3 L-glass reactor equipped with a stirrer was continuously charged with the reaction mixture containing 2-hydroxy-4-methylthiobutanamide and 2-hydroxy-4-methylthiobutanoic acid as obtained in hydration step (1A) through a hydration reaction mixture feed line 12 at a flow rate of 2,983 g/hr. On the other hand, an 8% aqueous solution of sodium hydroxide containing a small amount of sodium 2-hydroxy-4-methylthiobutanoate (a mixture of the aqueous solution of sodium hydroxide available from electrodialysis step (2) and the aqueous layer available from carboxylic acid extraction step (8)) was fed from base-water feed line 15 at a flow rate of 540 g/hr. In this manner, the hydrolysis reaction was carried out at a reaction temperature of 60° C.

As a result, a reaction mixture containing sodium 2-hydroxy-4-methylthiobutanoate (230 g/hr.), ammonia (17 g/hr.), water, and methyl ethyl ketone was obtained at a flow rate of 1,390 g/hr.

Ammonia recovery and concentration steps (6, 5)

A single-stage distillation column was continuously charged with the reaction mixture available from hydrolysis step (1B) through a hydrolyzate mixture feed line 16 at a flow rate of 3,520 g/hr. (sodium 2-hydroxy-4-methylthiobutanoate 230 g/hr., ammonia 17 g/hr.) to remove water (2,130 g/hr.) and ammonia (17 g/hr.). As a result, an aqueous solution containing sodium 2-hydroxy-4-methylthiobutanoate was obtained at a flow rate of 1,373 g/hr. (230 g/hr. as sodium 2-hydroxy-4-methylthiobutanoate).

The aqueous ammonia obtained as a distillate was stripped with methane gas in the same manner as in the ammonia recovery step according to Example 1 to recover ammonia. The recovered ammonia and methane gas were fed to a prussic acid production line. The water after removal of ammonia was reused in hydration step (1A).

Electrodialysis step (2), carboxylic acid extraction step (8), and carboxylic acid separating step (9)

The aqueous solution containing sodium 2-hydroxy-4-methylthiobutanoate as obtained in the ammonia recovery-concentration stage was subjected to electrodialysis step, carboxylic acid extraction step, and carboxylic acid separating step as in Example 1 to provide 2-hydroxy-4-methylthiobutanoic acid.

The sodium hydroxide available from electrodialysis step (2) was reused in hydrolysis step (1B) as in Example 1.

Example 3

2-Hydroxy-4-methylthiobutanoic acid was produced in accordance with Route (iv) in the production flow illustrated in FIG. 2.

Carboxylic acid salt providing step (1)

A loopful of Bacteridium sp. R341 (FERM P-2719) from a slant culture was used to inoculate 1,000 ml/Sakaguchi flask of the same liquid medium as used in Example 1 and shake-cultured aerobically at 30° C. for 48 hours.

The cultured cells were harvested by centrifuging the culture broth and washed 3 times each with a portion of 0.05 M phosphate buffer (pH 7.0). The washed cells were resuspended in 250 ml of the same buffer as above. Then, 2-hydroxy-4-methylthiobutyronitrile was added in a final concentration of 330 mM and the reaction was carried out at 5° C. for 24 hours. After completion of the reaction, the reaction mixture was centrifuged to remove the cells and provide a supernatant. Analysis of the supernatant by liquid chromatography revealed that it contained 4.9 weight %, on a free acid basis, of ammonium 2-hydroxy-4-methylthiobutanoate.

Concentration step (5)

A single-stage distillation column was charged with the reaction mixture available from carboxylic acid salt providing step (1) to remove water and thereby provide a concentrate containing ammonium 2-hydroxy-4-methylthiobutanoate.

Electrodialysis step (2), carboxylic acid extraction step (8), and carboxylic acid separating step (9)

The concentrate containing sodium 2-hydroxy-4-methylthiobutanoate as obtained in the concentration step (5) was fed to electrodialysis step, carboxylic acid extraction step, and carboxylic acid separating step as in Example 1 to provide 2-hydroxy-4-methylthiobutanoic acid.

Ammonia recovery step (6)

The aqueous ammonia obtained in the electrodialysis step (2) was fed to an ammonia stripping column and the procedure of the ammonia recovery step in Example 1 was repeated to provide an ammonia-methane mixture gas. This mixture gas was fed to a production line for prussic acid which is a starting compound for 2-hydroxy-4-methylthiobutyronitrile.

What is claimed is:

1. A method of producing a carboxylic acid which comprises (1) a carboxylic acid salt providing step comprising permitting a strain of microorganism capable of hydrating nitrites or a preparation derived from said microorganism to act upon a nitrile to thereby (a) provide at least the corresponding amide which is then hydrolyzed in the presence of a base to provide a salt of the corresponding carboxylic acid or (b) provide a salt of the corresponding carboxylic acid and (2) an electrodialysis step comprising subjecting the carboxylic acid salt provided in said carboxylic acid salt providing step to electrodialysis to provide the corresponding carboxylic acid and base.

2. A method of producing a carboxylic acid as claimed in claim 1, wherein the nitrile is a cyanohydrin compound.

3. A method of producing a carboxylic acid as claimed in claim 1, wherein the microorganism capable of hydrating nitrites is at least one strain of microorganism selected from the group consisting of the genus Pantoea, the genus Micrococcus, the genus Bacteridium, the genus Bacillus, the genus Actinomadura, the genus Kitasatospora, the genus Pilimelia, the genus Achromobacter, the genus Beijerinckia, the genus Cellulomonas, the genus Klebsiella, the genus Actinopolispora, the genus Actinosynnema, the genus Actinopulanes, the genus Amycolata, the genus Saccharopolyspora, the genus Streptomyces, the genus Nocardioides, the genus Providencia, the genus Microbacterium, the genus Rhodobacter, the genus Rhodospirillum, the genus Caseobacter, the genus Pseudomonas, the genus Alcaligenes, the genus Corynebacterium, the genus Brevibacterium, the genus Nocardia, the genus Rhodococcus, the genus Arthrobacter, the genus Torulopsis, the genus Rhodopseudomonas, the genus Acinetobacter, the genus Mycobacterium, the genus Candida, the genus Agrobacterium, the genus Aspergillus, the genus Penicillium, the genus Cochliobolus, the genus Fusarium, the genus Enterobacter, the genus Xanthobacter, the genus Erwinia, the genus Citrobacter, the genus Aeromonas, and the genus Gordona.

4. A method of producing a carboxylic acid as claimed in claim 1, wherein a strain of microorganism grown in the presence of at least one inducer selected from the group consisting of nitrites and amides is used as said strain of microorganism.

5. A method of producing a carboxylic acid as claimed in claim 1, wherein (a) nitrile hydratase, (b) nitrile hydratase and amidase, or (c) nitrilase is used as said preparation derived from the microorganism.

6. A method of producing a carboxylic acid as claimed in claim 1, wherein the base is an alkali metal hydroxide.

7. A method of producing a carboxylic acid as claimed in claim 1, wherein said electrodialysis is carried out using an electrodialyzer comprising a bipolar membrane and at least one ion exchange membrane selected from the group consisting of cation exchange membranes and anion exchange membranes.

8. A method of producing a carboxylic acid as claimed in claim 1, further comprising (3) a step of recycling the reaction mixture obtained by permitting said strain of microorganism or said preparation derived therefrom to act upon the nitrile to the hydration reaction system of the carboxylic acid salt providing step.

9. A method of producing a carboxylic acid as claimed in claim 1, further comprising (4) an amide extraction step for extracting the amide into an organic solvent from the amide-containing reaction mixture obtainable by permitting said microorganism or said preparation derived therefrom to act upon the nitrile.

10. A method of producing a carboxylic acid as claimed in claim 1, further comprising (5) a concentration step for concentrating (a) a reaction mixture containing the amide or carboxylic acid salt provided by permitting said microorganism or said preparation derived therefrom to act upon the nitrile or (b) a reaction mixture containing the carboxylic acid salt available upon hydrolysis of said amide.

11. A method of producing a carboxylic acid as claimed in claim 1, further comprising (6) an ammonia recovery step for recovering ammonia byproduced in said carboxylic acid salt providing step (1) or, in addition to said step (6), (7) a step for utilizing recovered ammonia as a nitrogen source in a nitrile production line.

12. A method of producing a carboxylic acid as claimed in claim 1, further comprising (8) a carboxylic acid extraction step for extracting the carboxylic acid from a solution containing the carboxylic acid and water as provided in electrodialysis step (2) into an organic solvent and either (9) a carboxylic acid separating step comprising separating the carboxylic acid from the organic solvent in the organic phase provided in carboxylic acid extraction step (8) or, in addition to said steps (8) and (9), (10) a step for recycling the organic solvent separated in carboxylic acid separating step (9) for reuse as an extraction solvent in carboxylic acid extraction step (8) or amide extraction step (4).

13. A method of producing a carboxylic acid as claimed in claim 9, wherein at least one hydrophobic organic solvent selected from the group consisting of alcohols, ketones, aldehydes, esters, and ethers is used as the organic solvent for extraction.

14. A method of producing a carboxylic acid as claimed in claim 1, further comprising (11) a step of reusing the base provided in electrodialysis step (2) as the base in carboxylic acid salt providing step (1).

15. A method of producing a carboxylic acid as claimed in claim 1, further comprising (12) a step in which the ammonium carboxylate formed in carboxylic acid salt providing step (1) is subjected to salt exchange with a base.

16. A method of producing a carboxylic acid which comprises (1) a hydration step comprising permitting a strain of microorganism capable of hydrating cyanohydrin compounds to at least the corresponding hydroxamides or a preparation derived from said microorganism to act upon a cyanohydrin compound to provide the corresponding hydroxamide and (2) an amide extraction step comprising extracting the reaction mixture containing said hydroxamide with an organic solvent to provide an organic phase containing the hydroxamide, (3) a hydrolysis step comprising hydrolyzing said hydroxamide of the organic phase in the presence of an alkali metal hydroxide to provide the corresponding alkali metal hydroxycarboxylate and ammonia, (4) an ammonia recovery-aqueous phase separating step for recovering ammonia and separating an aqueous phase containing said alkali metal hydroxycarboxylate from a mixture containing the alkali metal hydroxycarboxylate and ammonia as provided in said hydrolysis step (3), (5) an electrodialysis step comprising subjecting an aqueous phase containing said alkali metal hydroxycarboxylate as provided in said ammonia recovery-aqueous phase separating step (4) to electrodialysis using an electrodialyzer comprising a bipolar membrane and at least one ion exchange membrane selected from the group consisting of cation exchange membranes and anion exchange membranes to provide the corresponding hydroxycarboxylic acid and alkali metal hydroxide, (6) a step of recycling the ammonia recovered in said ammonia recovery-aqueous phase separating step (4) for reuse to a production line for hydrogen cyanide to be used as a starting material for cyano-hydrin compounds, and (7) a step of reusing the alkali metal hydroxide provided in said electrodialysis step (5) in hydrolysis step (3).

17. A method of producing a carboxylic acid as claimed in claim 16, further comprising at least one step selected from the group consisting of (8) a step of recycling the aqueous phase provided in amide extraction step (2) to hydration step (1) and (9) a step of effecting separation of the aqueous phase in ammonia recovery-aqueous phase separating step (4) by means of phase separation and recycling the organic phase to amide extraction step (2).

18. A method of producing a carboxylic acid which comprises (1) a hydration step comprising permitting a strain of microorganism capable of hydrating cyanohydrin compounds to the corresponding hydroxamides and hydroxycarboxylic acids or a preparation derived from said microorganism to act upon a cyanohydrin compound to provide the corresponding hydroxamide and hydroxycarboxylic acid ammonium salt, (2) a step of treating the reaction mixture containing said hydroxamide and hydroxycarboxylic acid ammonium salt with an alkali metal hydroxide to hydrolyze the hydroxamide and, at the same time, cause the hydroxycarboxylic acid ammonium salt, by salt exchange, to provide the corresponding alkali metal hydroxycarboxylate and ammonia (3) an ammonia recovery-concentration step comprising recovering ammonia from a reaction mixture containing said alkali metal hydroxycarboxylate and ammonia as provided in said hydrolysis step (2) and concentrating the mixture, (4) an electrodialysis step comprising subjecting the alkali metal hydrdxycarboxylate-containing mixture provided in said ammonia recovery-concentration step (3) to electrodialysis using an electrodialyzer comprising a bipolar membrane and at least one ion exchange membrane selected from the group consisting of cation exchange membranes and anion exchange membranes to provide the corresponding hydroxycarboxylic acid and alkali metal hydroxide, (5) a step of recycling the ammonia recovered in said ammonia recovery-concentration step (3) for reuse to a hydrogen cyanide production line as a starting material for cyanohydrin compounds, and (6) a step of reusing the alkali metal hydroxide available from said electrodialysis step (4) in hydrolysis step (2).

19. A method of producing a carboxylic acid which comprises (1) a carboxylic acid salt providing step comprising permitting a strain of microorganism capable of hydrating cyanohydrin compounds to at least. the corresponding hydroxycarboxylic acids or a preparation derived from said microorganism to act upon a cyanohydrin compound for conversion thereof to the corresponding ammonium hydroxycarboxylate (2) a salt exchange step comprising treating said ammonium hydroxycarboxylate with an alkali metal hydroxide to provide the corresponding alkali metal hydroxycarboxylate, (3) an ammonia recovery step for recovering the ammonia produced in said salt exchange step (4) a concentration step for concentrating the hydroxycarboxylate-containing mixture either in a stage upstream of said salt exchange step (2) or in a stage upstream or downstream of said ammonia recovery step (3), (5) an electrodialysis step comprising subjecting the alkali metal hydroxycarboxylate-containing mixture to electrodialysis using an electrodialyzer comprising a bipolar membrane and at least one ion exchange membrane selected from cation exchange membranes and anion exchange membranes to provide the corresponding free hydroxycarboxylic acid and alkali metal hydroxide, (6) a step of recycling the ammonia recovered in said ammonia recovery-step (3) for reuse to a hydrogen cyanide production line as a starting material for cyanohydrin compounds, and (7) a step of reusing the alkali metal hydroxide provided in said electrodialysis step (5) in said salt exchange step (2).

20. A method of producing a carboxylic acid which comprises (1) a carboxylic acid salt providing step comprising permitting a strain of microorganism capable of hydrating cyanohydrin compounds to at least the corresponding hydroxycarboxylic acids or a preparation derived from said microorganism to act upon a cyanohydrin compound to provide the corresponding ammonium hydroxycarboxylate, (2) a concentration step for concentrating the resulting ammonium hydroxycarboxylate-containing mixture, (3) an electrodialysis step comprising subjecting the concentrate provided in said concentration step (2) to electrodialysis using an electrodialyzer comprising a bipolar membrane and at least one ion exchange membrane selected from the group consisting of cation exchange membranes and anion exchange membranes to provide the free hydroxycarboxylic acid and ammonia, (4) an ammonia recovery step for recovering the ammonia produced in said electrodialysis step (3), and (5) a step of recycling the ammonia recovered in said ammonia recovery step (4) for reuse to a hydrogen cyanide production line as a starting material for cyanohydrin compounds.

21. A method of producing a carboxylic acid as claimed in claim 16, further comprising at least one step selected from the group consisting of (10) a step of recycling the reaction mixture obtained by permitting said strain of microorganism or said preparation derived therefrom to act on said cyanohydrin to the hydration reaction system, (11) a carboxylic acid extraction step for extracting the hydroxycarboxylic acid into an organic solvent from a mixture containing said hydroxycarboxylic acid and water as provided in electrodialysis step (5), and (12) a carboxylic acid separating step comprising separating the hydroxycarboxylic acid and the organic solvent from the organic phase provided in carboxylic acid extraction step (11).

22. A method of producing a carboxylic acid as claimed in claim 21, further comprising at least one step selected from the group consisting of (13) a step of recycling the aqueous phase provided in carboxylic acid extraction step (11) to hydrolysis step (3) or electrodialysis step (5), and (14) a step of reusing the organic solvent recovered in carboxylic acid separating step (12) as an extraction solvent in carboxylic acid extraction step (11) or amide extraction step (2).

23. A method of producing a carboxylic acid as claimed in claim 18, further comprising (7) a step of recycling the distillate water in the ammonia recovery-concentration step (3) to hydration step (1).

24. A method of producing a carboxylic acid as claimed in claim 16, wherein the cyanohydrin compound is a compound of the following formula (Ia),

 (Ia)

wherein $R^1$ and $R^2$ are the same or different and each represents a hydrogen atom or a hydrocarbon group which may optionally be substituted; $R^1$ and $R^2$ may jointly form a ring in association with the adjacent carbon atom; provided that when $R^1$ is a hydrogen atom, $R^2$ does not represent a hydrogen atom and vice versa.

25. A method of producing a carboxylic acid as claimed in claim 24, wherein $R^1$ and $R^2$ in formula (Ia) are the same or different and each represents $C_{1-12}$ alkyl, $C_{2-12}$ alkenyl, $C_{2-12}$ alkinyl, $C_{3-10}$ cycloalkyl, $C_{6-14}$ aryl, or $C_{7-10}$ aralkyl.

26. A method of producing a carboxylic acid as claimed in claim 24, wherein the cyanohydrin compound is 2-hydroxy-4-methylthiobutanenitrile.

* * * * *